(12) United States Patent
Yaghi et al.

(10) Patent No.: US 8,691,748 B2
(45) Date of Patent: Apr. 8, 2014

(54) EDIBLE AND BIOCOMPATIBLE METAL-ORGANIC FRAMEWORKS

(75) Inventors: Omar M. Yaghi, Los Angeles, CA (US); Oussama M. El-Kadri, Mississauga (CA); Qianrong Fang, Riverside, CA (US); Qiaowei Li, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 709 days.

(21) Appl. No.: 12/680,141

(22) PCT Filed: Sep. 25, 2008

(86) PCT No.: PCT/US2008/077741
§ 371 (c)(1),
(2), (4) Date: Jun. 23, 2010

(87) PCT Pub. No.: WO2009/042802
PCT Pub. Date: Apr. 2, 2009

(65) Prior Publication Data
US 2010/0286022 A1 Nov. 11, 2010

Related U.S. Application Data

(60) Provisional application No. 60/975,089, filed on Sep. 25, 2007.

(51) Int. Cl.
*A61K 38/00* (2006.01)
*A01N 25/00* (2006.01)
*A61K 47/00* (2006.01)

(52) U.S. Cl.
USPC .......................................... 514/1.1; 514/785

(58) Field of Classification Search
None
See application file for complete search history.

(56) References Cited

U.S. PATENT DOCUMENTS

| | | | |
|---|---|---|---|
| 4,532,225 A | 7/1985 | Tsao et al. | |
| 5,064,804 A * | 11/1991 | Soo et al. | 502/335 |
| 5,160,500 A | 11/1992 | Chu et al. | |
| 5,208,335 A | 5/1993 | Ramprasad et al. | |
| 5,648,508 A | 7/1997 | Yaghi et al. | |
| 6,479,447 B2 | 11/2002 | Bijl et al. | |
| 6,501,000 B1 | 12/2002 | Stilbrany et al. | |
| 6,617,467 B1 | 9/2003 | Muller et al. | |
| 6,624,318 B1 | 9/2003 | Mueller et al. | |
| 6,893,564 B2 | 5/2005 | Mueller et al. | |
| 6,929,679 B2 | 8/2005 | Mueller et al. | |
| 6,930,193 B2 | 8/2005 | Yaghi et al. | |
| 7,196,210 B2 | 3/2007 | Yaghi et al. | |
| 7,202,385 B2 | 4/2007 | Mueller et al. | |
| 7,279,517 B2 | 10/2007 | Mueller et al. | |
| 7,309,380 B2 | 12/2007 | Mueller et al. | |
| 7,343,747 B2 | 3/2008 | Mueller et al. | |
| 7,411,081 B2 | 8/2008 | Mueller et al. | |
| 7,524,444 B2 | 4/2009 | Hesse et al. | |
| 7,582,798 B2 | 9/2009 | Yaghi et al. | |
| 7,652,132 B2 | 1/2010 | Yaghi et al. | |
| 7,662,746 B2 | 2/2010 | Yaghi et al. | |
| 7,799,120 B2 | 9/2010 | Yaghi et al. | |
| 7,815,716 B2 * | 10/2010 | Mueller et al. | 95/90 |
| 8,501,150 B2 * | 8/2013 | Schubert et al. | 423/625 |
| 8,518,264 B2 * | 8/2013 | Kiener et al. | 210/660 |
| 8,524,932 B2 * | 9/2013 | Leung et al. | 556/183 |
| 2003/0004364 A1 | 1/2003 | Yaghi et al. | |
| 2003/0078311 A1 | 4/2003 | Muller et al. | |
| 2003/0148165 A1 | 8/2003 | Muller et al. | |
| 2003/0222023 A1 | 12/2003 | Mueller et al. | |
| 2004/0081611 A1 | 4/2004 | Muller et al. | |
| 2004/0225134 A1 | 11/2004 | Yaghi et al. | |
| 2004/0249189 A1 | 12/2004 | Mueller et al. | |
| 2004/0265670 A1 | 12/2004 | Muller et al. | |
| 2005/0004404 A1 | 1/2005 | Muller et al. | |
| 2005/0014371 A1 | 1/2005 | Tsapatsis | |
| 2005/0124819 A1 | 6/2005 | Yaghi et al. | |
| 2005/0154222 A1 | 7/2005 | Muller et al. | |
| 2005/0192175 A1 | 9/2005 | Yaghi et al. | |
| 2006/0057057 A1 | 3/2006 | Muller et al. | |
| 2006/0135824 A1 | 6/2006 | Mueller et al. | |
| 2006/0154807 A1 | 7/2006 | Yaghi et al. | |
| 2006/0185388 A1 * | 8/2006 | Muller et al. | 62/606 |
| 2006/0252641 A1 * | 11/2006 | Yaghi et al. | 502/401 |
| 2006/0252972 A1 | 11/2006 | Pilliod et al. | |
| 2006/0287190 A1 | 12/2006 | Eddaoudi et al. | |
| 2007/0068389 A1 | 3/2007 | Yaghi et al. | |

(Continued)

FOREIGN PATENT DOCUMENTS

| | | |
|---|---|---|
| DE | 102005023856 A1 | 11/2006 |
| DE | 102005054523 A1 | 5/2007 |

(Continued)

OTHER PUBLICATIONS

Sigma-Aldrich, Citric acid, ACS reagent. Accessed online on Oct. 30, 2012 at http://www.sigmaaldrich.com/catalog/product/sial/251275?lang=en&region=US, 2 pages.*
Wardencki et al. Green Chemistry—Current and Future Issues. Review. Polish Journal of Environmental Studies. 2005. vol. 14, No. 4, pp. 389-395.*
Serre et al. A Route to the Synthesis of Trivalent Transition-Metal Porous Carboxylates with Trimeric Secondary Building Units. Angew Chem Int Ed 2004 vol. 43, pp. 6285-6289.*
Serre et al. A Route to the Synthesis of Trivalent Transition-Metal Porous Carboxylates with Trimeric Secondary Building Units. Angew Chem Int Ed 2004 vol. 116, pp. 6445-6449.*
Surble et al. A new isoreticular class of metal-organic-frameworks with the MIL-88 topology. Chem Commun, 2006, pp. 284-286.*
Whitfield et al. Metal-organic frameworks based on iron oxide octahedral chains connected by benzendicarboxylate dianions. Solid State Sciences, 2005. vol. 7, pp. 1096-1103.*

(Continued)

*Primary Examiner* — Marcela M Cordero Garcia
(74) *Attorney, Agent, or Firm* — Joseph R. Baker, Jr.; Gavrilovich, Dodd & Lindsey LLP

(57) ABSTRACT

The disclosure relates generally to materials that comprise organic frameworks. The disclosure also relates to materials that are useful to store and separate biological agents that are environmentally friendly and biocompatible.

34 Claims, 9 Drawing Sheets

(56) References Cited

U.S. PATENT DOCUMENTS

| | | |
|---|---|---|
| 2007/0202038 A1 | 8/2007 | Yaghi et al. |
| 2007/0248575 A1* | 10/2007 | Connor et al. ............... 424/93.7 |
| 2008/0184883 A1 | 8/2008 | Zhou et al. |
| 2009/0155588 A1 | 6/2009 | Hesse et al. |
| 2010/0132549 A1 | 6/2010 | Yaghi et al. |
| 2010/0143693 A1 | 6/2010 | Yaghi et al. |
| 2010/0186588 A1 | 7/2010 | Yaghi et al. |
| 2011/0137025 A1 | 6/2011 | Yaghi et al. |

FOREIGN PATENT DOCUMENTS

| | | | |
|---|---|---|---|
| EP | 1674555 A1 | 6/2006 | |
| WO | 2004101575 A2 | 11/2004 | |
| WO | 2006072573 A2 | 7/2006 | |
| WO | 2006116340 A1 | 11/2006 | |
| WO | 2007101241 A2 | 9/2007 | |
| WO | 2007111739 A2 | 10/2007 | |
| WO | WO 2007/118843 * | 10/2007 | ............... C01G 1/02 |
| WO | 2008091976 A1 | 7/2008 | |
| WO | 2008138989 A1 | 11/2008 | |
| WO | 2008140788 A1 | 11/2008 | |
| WO | 2009020745 A9 | 2/2009 | |
| WO | 2009042802 A1 | 4/2009 | |
| WO | 2009149381 A2 | 12/2009 | |
| WO | 2010078337 A1 | 7/2010 | |
| WO | 2010080618 A1 | 7/2010 | |
| WO | 2010083418 A1 | 7/2010 | |
| WO | 2010088629 A1 | 8/2010 | |
| WO | 2010090683 A1 | 8/2010 | |
| WO | 2010148276 A3 | 12/2010 | |
| WO | 2010148296 A3 | 12/2010 | |
| WO | 2010148374 A3 | 12/2010 | |
| WO | 2011014503 A1 | 2/2011 | |
| WO | 2011038208 A2 | 3/2011 | |

OTHER PUBLICATIONS

Fang et al. A Metal-Organic Framework with the Zeolite MTN Topology Containing Large Cages of vol. 2.5 nm3. Ang Chem Int Ed 2005, vol. 44, pp. 3845-3848.*

Horcajada et al. Metal-Organic Framewoks as Efficient Materials for Drug Delivery. Angew Chem Int Ed, 2006, vol. 45, pp. 5974-5978.*

Yaghi et al., "Metal-Organic Frameworks: A Tale of Two Entanglements," Nature materials 6:92-93 (2007).

Yaghi et al., "Reticular Chemistry and Metal-Organic Frameworks for Clean Energy," MRS Bulletin 34:682-690 (2009).

Young, Jung Doo. International Search Report for PCT/US2010/050170. Date of Mailing: Jun. 8, 2011.

Zhang et al., "Docking in Metal-Organic Frameworks," Science 325:855-859 (2009).

Zhao et al., "Rigid-Strut-Containing Crown Ethers and [2]Catenanes for Incorporation into Metal-Organic Frameworks," Chem. Eur. J. 15:13356-13380 (2009).

Okeeffe et al., "Reticular Chemistry—Present and Future Prospects—Introduction," J. Solid State Chem.178:V-VI (2005).

O'Keeffe et al., "The Reticular Chemistry Structure Resource (RCSR) Database of, and Symbols for, Crystal Nets," Acc. Chem. Res. 41:1782-1789 (2008).

Park, Jae Woo. International Search Report for PCT/US2010/039123. Date of Mailing: Feb. 24, 2011.

Patteux, Claudine. International Search Report for PCT/US2010/043373. Date of Mailing: Oct. 10, 2010.

Peterson et al., "Ammonia Vapor Removal by Cu3(BTC)2 and Its Characterization by MAS NMR," J. Phys. Chem. C. 113(32):13906-13917 (2009).

Phan et al., "Synthesis, Structure, and Carbon Dioxide Capture Properties of Zeolitic Imidazolate Frameworks," Acc. Chem. Res 43:58-67 (2009).

Rosi et al., "Infinite Secondary Building Units and Forbidden Catenation in Metal-Organic Frameworks," Angew. Chem. Int. Ed. 41:294-297 (2002).

Rosi et al., "Advances in the Chemistry of Metal-Organic Frameworks," CrystEngComm 4:401-404 (2002).

Rosi et al., "Hydrogen Storage in Microporous Metal-Organic Frameworks," Science 300:1127-1129 (2003); Featured in (1) Chemical & Engineering News magazine, May 19, 2004, and (2) Technology Research News Magazine, May 21, 2003.

Rosi et al., "Rod-Packings and Metal-Organic Frameworks Constructed from Rod-Shaped Secondary Building Units," J. Am. Chem. Soc. 127:1504-1518 (2005).

Rowsell et al., "Hydrogen Sorption in Functionalized Metal-Organic Frameworks," J. Am. Chem. Soc.126: 5666-5667 (2004).

Rowsell et al., "Metal-Organic Frameworks: A New Class of Porous Materials," Microporous Mesoporous Mater. 73:3-14 (2004).

Rowsell et al., "Strategies for Hydrogen Storage in Metal-Organic Frameworks," Angew. Chem. Int. Ed. 44: 4670-4679 (2005).

Rowsell et al., "Gas Adsorption Sites in a Large-Pore Metal-Organic Framework," Science 309:1350-1354 (2005).

Rowsell et al., "Characterization of H2 Binding sites in prototypical metal-organic frameworks by inelastic neutron scattering," J. Am. Chem. Soc. 127:14904-14910 (2005).

Rowsell et al., "Effects of Functionalization, Catenation, and Variation of the Metal Oxide and Organic Linking Units on the Low-Pressure Hydrogen Adsorption Properties of Metal-Organic Frameworks," J. Am. Chem. Soc. 128: 1304-1315 (2006).

Seo et al., "A homochiral metal-organic porous material for enantioselective separation and catalysis," Nature 404:982-986 (2000).

Siberio-Perez, "Raman Spectroscopic Investigation of CH4 and N2 Adsorption in Metal-Organic Frameworks," Chem. Mater. 19:3681-3685 (2007).

Smaldone et al., "Metal-Organic Frameworks from Edible Nature Products," Angew. Chem. Int. Ed. 49:8630-8634 (2010).

Spencer et al., "Determination of the Hydrogen Absorption Sites in Zn4O(1,4-benzenedicarboxylate) by Single Crystal Neutron Diffraction," Chem. Commun. 3:278-280 (2006); Epub Dec. 6, 2005.

Stallmach et al., "NMR Studies on the Diffusion of Hydrocarbons on the Metal-Organic Framework Material MOF-5," Angew. Chem. Int. Ed. 45:2123-2126 (2006).

Sudik et al., "Design, Synthesis, Structure, and Gas (N2, Ar, CO2, CH4 and H2) Sorption Properties of Porous Metal-Organic Tetrahedral and Heterocuboidal Polyhedra," J. Am. Chem. Soc. 127:7110-7118 (2005).

Sudik et al., "Metal-Organic Frameworks Based on Trigonal Prismatic Building Blocks and the New "acs" Topology," Inorg. Chem. 44:2998-3000 (2005).

Sudik et al., "A Metal-Organic Framework with a Hierarchical System of Pores and Tetrahedral Bbuilding Blocks," Angew. Chem. Int. Ed. 45:2528-2533 (2006).

Tanabe et al., "Systematic Functionalization of a Metal-Organic Framework via a Postsynthetic Modification Approach," J. Am. Chem. Soc. 130(26):8508-8517 (2008).

Tranchemontagne et al. "Metal-Organic Frameworks with High Capacity and Selectivity for Harmful Gases," Proc. Natl. Acad. Sci. USA 105:11623-11627 (2008).

Tranchemontagne et al., "Reticular Chemistry of Metal-Organic Polyhedra," Angew. Chem. Int. Ed., 2008, 47:5136-5147 (2008).

Tranchemontagne et al., "Room Temperature Synthesis of Metal-organic Frameworks: MOF-5, MOF-74, MOF-177, MOF-199, and IRMOF-0," Tetrahedron 64:8553-8557 (2008).

Tranchemontagne et al. "Secondary Building Units, Nets and Bonding in the Chemistry of Metal-Organic Frameworks," Chem. Soc. Rev. 38:1257-1283 (2009).

Uribe-Romo et al., "A Crystalline Imine-Linked 3-D Porous Covalent Organic Framework," J. Am. Chem. Soc. 131:4570-4571 (2009).

Uribe-Romo et al., "Crystalline Covalent Organic Frameworks with Hydrazone Linkages," J. Am. Chem. Soc. 133: 11478-11481 (2011).

Vairaprakash et al., "Synthesis of Metal-Organic Complex Arrays," J. Am. Chem. Soc. 133:759-761 (2011).

Valente et al., "Metal-organic Frameworks with Designed Chiral Recognition Sites," Chem. Commun. 46: 4911-4913 (2010).

Vitillo et al., "Role of Exposed Metal Sites in Hydrogen Storage in MOFs," J. Am. Chem. Soc. 130(26):8386-8396 (2008).

(56) References Cited

OTHER PUBLICATIONS

Vodak et al., "Metal-Organic Frameworks Constructed from Pentagonal Antiprismatic and Cuboctahedral Secondary Building Units," Chem. Commun. 2534-2535 (2001).
Vodak et al., "One-Step Synthesis and Structure of an Oligo(spiroorthocarbonate)," J. Am. Chem. Soc.124 (18):4942-4943 (2002).
Vodak et al., "Computation of Aromatic C3N4 Networks and Synthesis of the Molecular Precursor N(C3N3)3C16," Chem. Eur. J. 9:4197-4201 (2003).
Walton et al., "Understanding Inflections and Steps in Carbon Dioxide Adsorption Isotherms in Metal-Organic Frameworks," J. Am. Chem. Soc.130:406-407 (2008).
Wang et al., "Postsynthetic Covalent Modification of a Neutral Metal-Organic Framework," J. Am. Chem. Soc. 129 (41):12368-12369 (2007).
Wang et al., "Tandem Modification of Metal-Organic Frameworks by a Postsynthetic Approach," Angew. Chem. Int. 47:4699-4702 (2008).
Wang et al., "Colossal Cages in Zeolitic Imidazolate Frameworks as Selective Carbon Dioxide Reservoirs," Nature 453:207-211 (2008).
Wong-Foy, Ag et al., "Exceptional H2 saturation uptake in microporous metal-organic frameworks" J. Am. Chem. Soc., 2006, 128, pp. 3494-3495.
Yaghi et al., "Selective binding and removal of guests in a microporous metal-organic framework," Nature, Dec. 1995, pp. 703-706, vol. 378.
Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.
Yaghi et al., "Presence of Mutually Interpenetrating Sheets and Channels in the Extended Structure of Cu(4,4'-Bipyridine)CI," Angew. Chem. Int. Ed. Engl., 1995, 34, 207-209.
Yaghi et al., "A Molecular World Full of Holes," Chem. Innov. p. 3 (2000).
Yaghi et al., "Reticular Synthesis and the Design of New Materials," Nature 423:705-714 (2003).
Yaghi, Omar., "Porous Crystals for Carbon Dioxide Storage," slide presentation at the Fifth Annual Conference on Carbon Capture & Sequestration, US Department of Energy on May 10, 2006 http://www.netl.doe.gov/publications/proceedings/06/carbon-seq/Tech%20Session%20193.pdf.
Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.
Andrew et al., "Post-Synthetic Modification of Tagged MOFs," Angew. Chem. Int. Ed. 47:8482-8486 (2008).
Baharlou, Simin. International Preliminary Report on Patentability for PCT/US2009/046463. Date of Mailing: Dec. 16, 2010.
Banerjee et al., "High-Throughput Synthesis of Zeolitic Imidazolate Frameworks and Application to CO2 Capture," Science 319:939-943 (2008).
Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009).
Barman et al., "Azulene Based Metal-Organic Frameworks for Strong Adsorption of H2," Chem. Commun. 46: 7981-7983 (2010).
Barton et al., "Tailored Porous Materials," Chem. Mater. 11:2633-2656 (1999).
Bloch et al., "Metal Insertion in a Microporous Metal-Organic Framework Lined with 2,2'-Bipyridine" J. Am. Chem. Soc. 132:14382-14384 (2010).
Braun et al., "1,4-Benzenedicarboxylate Derivatives as Links in the Design of Paddle-Wheel Units and Metal-Organic Frameworks," Chem. Commun. 24:2532-2533 (2001).
Britt et al., "Highly efficient separation of carbon dioxide by a metal-organic framework replete with open metal sites," Proc. Natl. Acad. Sci. USA 106:20637-20640 (2009).

Carlucci et al., "Nanoporous three-dimensional networks topologically related to cooperite from the self-assembly of copper(I)centres and 1,2,4,5-tetracyanobenzene," New J. Chem. 23(23):397-401 (1999).
Carlucci, Lucia et al., "Polycatenation, polythreading and polyknotting in coordination network chemistry" Coordination Chemistry Reviews 246, 2003, pp. 247-289.
Caskey et al., "Dramatic Tuning of CO2 Uptake via Metal Substitution in a Coordination Polymer with Cylindrical Pores," JACS 130(33):10870-10871 (2008).
Caskey et al., "Selected Applications of Metal-Organic Frameworks in Sustainable Energy Technologies," Material Matters 4.4:111 (2009).
Chae et al., "Tertiary Building Units: Synthesis, Structure, and Porosity of a Metal-Organic Dendrimer Framework (MOD-1)," J. Am. Chem. Soc. 123:11482-11483 (2001).
Chae et al., "Design of Frameworks with Mixed Triangular and Octahedral Building Blocks Exemplified by the Structure of [Zn4O(TCA)2] Having the Pyrite Topology," Angew. Chem. Int. Ed. 42:3907-3909 (2003).
Chae et al., "A Route to High Surface Area, Porosity and Inclusion of Large Molecules in Crystals," Nature427, 523-527 (2004); Featured in (1) Chemical & Engineering News magazine, Feb. 9, 2004, (2) BBC World Service, Feb. 04, (3) New Scientist, Feb. 04.
Chen et al., "Cu2(ATC)6H2O: Design of Open Metal Sites in Porous Metal-Organic Crystals (ATC: 1,3,5,7-adamantane tetracarboxylate)," J. Am. Chem. Soc. 122:11559-11560 (2000).
Chen et al., "Interwoven Metal-Organic Framework on a Periodic Minimal Surface with Extra-Large Pores," Science 291:1021-1023 (2001); Featured in Chemical and Engineering News, Feb. 21, 2001.
Chen et al., "High H2 Adsorption in a Microporous Metal-Organic Framework with Open-Metal Sites," Angew. Chem. Int. Ed. 44:4745-4749 (2005).
Choi et al., "Heterogeneity within Order in Crystals of a Porous Metal Organic Framework," J. Am. Chem. Soc. 133:11920-11923 (2011).
Costa et al., "Chemical Modification of a Bridging Ligand Inside a Metal-Organic Framework while Maintaining the 3D Structure," Eur. J. Inorg. Chem. 10:1539-1545 (2008).
Cote et al., "Porous, Crystalline, Covalent Organic Frameworks," Science 310:1166-1170 (2005).
Cote et al., "Reticular Synthesis of Microporous and Mesoporous 2D Covalent Organic Frameworks," J. Am. Chem. Soc. 129:12914-12915 (2007).
Cui et al., "IIn Situ Hydrothermal Growth of Metal-Organic Framework 199 Films on Stainless Steel Fibers for Solid-Phase Microextraction of Gaseous Benzene Homologues," Anal. Chem. 81(23):9771-9777 (2009).
Delgado-Friedrichs et al., "Three-Periodic Nets and Tilings: Regular and Quasiregular Nets," Acta Cryst. A59: 22-27 (2003).
Delgado-Friedrichs et al., "Three-Periodic Nets and Tilings: Semiregular Nets," Acta Cryst. A59:515-525 (2003).
Delgado-Friedrichs et al., "Reticular Chemistry: Occurrence and Taxonomy of Nets, and Grammar for the Design of Frameworks," Acc. Chem. Res. 38:176-182 (2005).
Delgado-Friedrichs et al. "What Do We Know About Three-Periodic Nets?," J. Solid State Chem. 178: 2533-2554 (2005).
Delgado-Friedrichs et al. "Three-Periodic Nets and Tilings: Edge-Transitive Binodal Structures," Acta Cryst. 62:350-355 (2006).
Delgado-Friedrichs et al., "Taxonomy of Periodic Nets and the Design of Materials," Phys. Chem. 9:1035-1043 (2007).
Deng et al., "Multiple Functional Groups of Varying Ratios in Metal-Organic Frameworks," Science 327:846-850 (2010).
Deng et al., "Robust dynamics" Nature Chem. 2:439-443 (2010).
Doonan et al., "Isoreticular Metalation of Metal-Organic Frameworks," J. Am. Chem. Soc. 131:9492-9493 (2009).
Doonan, C., "Hydrogen Storage in Metal-Organic Frameworks," Annual Merit Review Proceedings of DOE Hydrogen Program, May 22, 2009.
Doonan et al., "Exceptional ammonia uptake by a covalent organic framework," Nature Chem. 2:235-238 (2010).
Dugan et al., "Covalent modification of a metal-organic framework with isocyanates: probing substrate scope and reactivity," 29:3366-3368 (2008).

(56) References Cited

OTHER PUBLICATIONS

Duren et al., "Design of New Materials for Methane Storage," Langmuir 20:2683-2689 (2004).
Eddaoudi et al., "Design and Synthesis of Metal-Organic Frameworks with Permanent Porosity," In Topics in Catalysis, G. A. Somorjai and J. M. Thomas, Eds., 9:105 (1999).
Eddaoudi et al., "Highly Porous and Stable Metal-Organic Framework: Structure Design and Sorption Properties," J. Am. Chem. Soc. 121:1391-1397 (2000).
Eddaoudi et al., "Porous Metal-Organic Polyhedra: 25 Å Cuboctahedron Constructed from Twelve Cu2(CO2)4 Paddle-Wheel Building Blocks," J. Am. Chem. Soc. 123:4368-4369 (2001).
Eddaoudi et al., "Modular Chemistry: Secondary Building Units as a Basis for the Design of Highly Porous and Robust Metal-Organic Carboxylate Frameworks" Acc. Chem. Res. 34:319-330 (2001).
Eddaoudi et al., "Geometric Requirements and Examples of Important Structures in the Assembly of Square Building Blocks," Proc. Natl. Acad. Sci. 99:4900-4904 (2002).
Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.
Eddaoudi et al., "Cu2[o-Br-C6H3(CO2)2]2(H2O)2•(DMF)8(H2O)2: A Framework Deliberately Designed to have the NbO Structure Type," J. Am. Chem. Soc.124:376-377 (2002).
Furukawa et al., "Crystal Structure, Dissolution, and Deposition of a 5 nm Functionalized Metal-Organic Great Rhombicuboctahedron," J. Am. Chem. Soc. 128:8398-8399 (2006).
Furkawa et al., "Independent verification of the saturation hydrogen uptake in MOF-177 and establishment of a benchmark for hydrogen adsorption in metal-organic frameworks," J. Mater. Chem. 17:3197-3204 (2007).
Furukawa et al., "Control of Vertex Geometry, Structure Dimensionality, Functionality, and Pore Metrics in the Reticular Synthesis of Crystalline Metal-Organic Frameworks and Polyhedra," J. Am. Chem. Soc.130:11650-11661 (2008).
Furukawa et al., "Storage of Hydrogen, Methane, and Carbon Dioxide in Highly Porous Covalent Organic Frameworks for Clean Energy Applications," J. Am. Chem. Soc. 25:8876-8883 (2009).
Furukawa et al., "Ultra-High Porosity in Metal-Organic Frameworks," Science 239:424-428 (2010).
Galli et al., "Adsorption of Harmful Organic Vapors by Flexible Hydrophobic Bis-pyrazolate Based MOFs," Chem. Mater. 22(5):1664-1672 (2010).
Ashton, Peter R. et al., "Hydrogen-Bonded Complexes of Aromatic Crown Ethers with (9-Anthracenyl) methylammonium Derivatives" J. Am. Chem. Soc., 1997, 119 (44), pp. 10641-10651.
Carlucci, Lucia et al., "Polycatenation, polythreading and polyknotting in coordination network chemistry" Coordination Chemistry Reviews 246, 2003, pp. 247-289, Elsevier.
Han, SS et al., "Improved designs of metal-organic frameworks for hydrogen storage" Angew. Chem. Int. Ed. 2007, 46, pp. 6289-6292.
Kim, Su Mi, International Search Report and Written Opinion, Date of Mailing: Feb. 24, 2010, International Application No. PCT/US09/46463.
Loeb, SJ, "Rotaxanes as ligands: from molecules to materials" Chemical Society reviews, 2007, 36, pp. 226-235.
Moyse, Ellen, International Preliminary Report on Patentability and Written Opinion, Date of Issuance of Report: Nov. 17, 2009, International Application No. PCT/US08/006008.
Nickitas-Etienne, Athina, International Preliminary Report on Patentability and Written Opinion, Date of Issuance of Report: Jan. 19, 2010, International Application No. PCT/US08/70149.
Park, Kyo Sung et al., "Exceptional chemical and thermal stability of zeolitic imidazolate frameworks," Proc. Natl. Acad. Sci., Jul. 5, 2006, pp. 10186-10191, vol. 103, No. 27.
Young, Lee W., International Search Report and Written Opinion, Date of Mailing: Dec. 2, 2008, International Application No. PCT/US08/77741.
Young, Lee W., International Search Report and Written Opinion, Date of Mailing: Jan. 12, 2009, International Application No. PCT/US08/70149.
Young, Lee W., International Search Report and Written Opinion, Date of Mailing of Report: May 7, 2008, International Application No. PCT/US08/51859.
Young, Lee W., "International search Report and Written Opinion," PCT/US08/06008, United States Patent & Trademark Office, Aug. 20, 2008.
Glover et al., "MOF-74 building unit has a direct impact on toxic gas adsorption," J. Chem. Eng. Sci. 66:163-170 (2011).
Gould et al., "The Amphidynamic Character of Crystalline MOF-5: Rotational Dynamics in a Free-Volume Environment," J. Am. Chem. Soc. 130:3246-3247 (2008).
Goebel, Matthias, Supplemental European Search Report and Written Opinion for EP08826913. Date of Completion of Search and Written Opinion: Nov. 10, 2010.
Goebel, Matthias, Supplemental European Search Report and Written Opinion for EP08754337. Date of Completion of Search and Written Opinion: Dec. 3, 2010.
Grzesiak et al., "Polymer-Induced Heteronucleation for the Discovery of New Extended Solids," Angew. Chem. Int. Ed. 45:2553-2556 (2006).
Halper et al., "Topological Control in Heterometallic Metal-Organic Frameworks by Anion Templating and Metalloligand Design," J. Am. Chem. Soc. 128:15255-15268 (2006).
Han et al., "Covalent Organic Frameworks as Exceptional Hydrogen Storage Materials," J. Am. Chem. Soc. 130: 11580-11581 (2008).
Hayashi et al., "Zeolite A Imidazolate Frameworks," Nature Materials 6:501-506 (2007).
Hexiang et al., "Multiple Functional Groups of Varying Rations in Metal-Organic Frameworks," Science 327 (5967):846-850 (2010).
Honda, Masashi, International Preliminary Report on Patentability for PCT/US2008/051859. Date of Issuance of the Report: Jul. 28, 2009.
Howe, Patrick. International Search Report and Written Opinion for PCT/US2009/068849. Date of Mailing of the Search Report: Jun. 4, 201.
Howe, Patrick. International Search Report and Written Opinion for PCT/US2010/022777. Date of Mailing: Jun. 7, 2010.
Huang et al., "Thermal Conductivity of Metal-Organic Framework 5 (MOF-5): Part II. Measurement," Int. J. Heat Mass Transfer 50:405-411 (2007).
Hunt et al., "Reticular Synthesis of Covalent Organic Borosilicate Frameworks," J. Am. Chem. Soc. 130: 11872-11873 (2008).
Ingleson et al., "Framework fractionalization triggers metal complex binding," Chem. Comm. 23:2680-2682 (2008).
Isaeva et al., "Metal-organic frameworks-new materials for hydrogen storage," Russian Journal of General Chemistry 77(4):721-739(2007).
Kaderi et al., "Designed Synthesis of 3D Covalent Organic Frameworks," Science 316:268-272 (2007).
Kaye et al., "Impact of Preparation and Handling on the Hydrogen Storage Properties of Zn4O(1,4-benzenedicarboxylate)3 (MOF-5)," J. Am. Chem. Soc. 129:14176-14177 (2007).
Kim et al., "Assembly of Metal-Organic Frameworks From Large Organic and Inorganic Secondary Building Units: New Examples and Simplifying Principles for Complex Structures," J. Am. Chem. Soc. 123:8239-8247 (2001).
Kim, Su Mi, International Search Report and Written Opinion for PCT/US2009/068731. Date of Mailing: Aug. 19, 2010.
Kim, Su Mi. International Search Report for PCT/US2010/039154. Date of Mailing: Feb. 23, 2011.
Klaes, Daphne. International Search Report and Written Opinion for PCT/US2010/021201. Date of Mailing: Apr. 27, 2010.
Kyoungmoo et al., "A Crystalline Mesoporous Coordination Copolymer with High Microporosity," Angew. Chem. Int. Ed. 47(4):677-680 (2008).
Lee, Ji Min. International Search Report for PCT/US2010/039284. Date of Mailing: Feb. 22, 2011.

(56) References Cited

OTHER PUBLICATIONS

Li et al., "Coordinatively Unsaturated Metal Centers in the Extended Porous Framewokr of Zn3(BDC)3-6CH3OH (BDC= 1,4-Benzenedicarboxylate)," J. Am. Chem. Soc. 2186-2187 (1998).

Li et al., "Design and Synthesis of an Exceptionally Stable and Highly Porous Metal-Organic Framework," Science 402:276-279 (1999); Featured in (1) Chemical and Engineering News (Nov. 22, 1999) and (2) Science News (Nov. 20, 1999).

Li et al., "A metal-organic framework replete with ordered donor-acceptor catenanes," Chem. Commun. 46:380-382 (2010).

Li et al., "A Catenated Strut in a Catenated Metal-Organic Framework," Angew. Chem. Int. Ed. 49:6751-6755 (2010).

Linder, Nora. International Preliminary Report on Patentability for PCT/US2010/022777. Date of Mailing: Aug. 11, 2011.

Llabres et al., "MOFs as catalysts: Activity, reusability and shape-selectivity of a Pd-containing MOF," JOurnal of Catalysis 250(2):294-298.

Long et al., "The Pervasive Chemistry of Metal-Organic Frameworks," Chem. Soc. Rev. 38:1213-1214 (2009).

Lu et al., "Synthesis and Structure of Chemically Stable Metal-Organic Polyhedra," J. Am. Chem. Soc. 131:(35) 12532-12533 (2009).

Mendoza-Cortes et al., "Adsorption Mechanism and Uptake of Methane in Covalent Organic Frameworks: Theory and Experiment," J. Phys. Chem. 114:10824-10833 (2010).

Michalitsch, Richard. International Search Report and Written Opinion for PCT/US2009/069700. Date of Mailing: May 7, 2010.

Millward et al., "Metal-Organic Frameworks with Exceptionally High Capacity for Storage of Carbon Dioxide at Room Temperature," J. Am. Chem. Soc. 127:17998-17999 (2005).

Morris et al., "Crystals as Molecules: Postsynthesis Covalent Functionalization of Zeolitic Imidazolate Frameworks," J. Am. Chem. Soc. 130:12626-12627 (2008).

Morris et al., "A Combined Experimental-Computational Investigation of Carbon Dioxide Capture in a Series of Isoreticular Zeolitic Imidazolate Frameworks," J. Am. Chem. Soc. 132:11006-11008 (2010).

Morris et al., "Postsynthetic Modification of a Metal-Organic Framework for Stabilization of a Hemiaminal and Ammonia Uptake," Inorg. Chem. 50:6853-6855 (2011).

Mulhausen, Dorothee. International Preliminary Report on Patentability for PCT/US2009/069700. Date of Mailing: Jul. 7, 2011.

Mulhausen, Dorothee. International Preliminary Report on Patentability for PCT/US2010/021201. Date of Mailing Jul. 28, 2011.

Natarajan et al., "Non-carboxylate based metal-organic frameworks (MOFs) and related aspects," Current Opinion in Solid State and Materials Science 13(3-4):46-53 (2009).

Ni et al,. "Porous Metal-Organic Truncated Octahedron Constructed from Paddle-Wheel Squares and Terthiophene Links," J. Am. Chem. Soc. 127:12752-12753 (2005).

Nickitas-Etienne, Athina. International Preliminary Report on Patentability for PCT/US2008/07741. Date of issuance of this report: Mar. 30, 2010.

Nickitas-Etienne, Athina, International Preliminary Report on Patentability for PCT/US2009/068731. Date of Issuance of the Report: Jun. 21, 2011.

Nickitas-Etienne, Athina. International Preliminary Report on Patentability for PCT/US2009/068849. Date of Mailing: Jun. 30, 2011.

Oisaki et al., "A Metal-Organic Framework with Covalently Bound Organometallic Complexes," J. Am. Chem. Soc. 132:9262-9264 (2010).

O'Keefe et al., "Frameworks for Extended Solids: Geometrical Design Principles," J. Solid State Chem. 152:3-20 (2000).

\* cited by examiner

PXRD of $[Mg_3(Citrate)_2(H_2O)_6]8H_2O$

PXRD of $[Ca(Mal)]2H_2O$

EDIBLE AND BIOCOMPATIBLE METAL-ORGANIC FRAMEWORKS

CROSS-REFERENCE TO RELATED APPLICATIONS

This application is a U.S. National Stage Application filed under 35 U.S.C. §371 and claims priority to International Application No. PCT/US08/77741, filed Sep. 25, 2008, which application claims priority under 35 U.S.C. §119 to U.S. Provisional Application Ser. No. 60/975,089, filed Sep. 25, 2007, the disclosures of which are incorporated herein by reference.

FIELD OF THE DISCLOSURE

The disclosure relates generally to materials that comprised metal organic frameworks. The disclosure also relates to materials that are useful to deliver molecules in a biological system as well as biological sensors.

BACKGROUND

Existing metal organic frameworks are toxic and lack biocompatibility.

SUMMARY

The disclosure provides porous biocompatible metal organic frameworks (bMOFs) developed from non-toxic starting materials. Such bMOF materials can be utilized in drug storage and delivery, flavoring and drying agents in food, catalysis, tissue engineering, dietary supplements, separation technology and gas storage.

The disclosure provides routes for the design and synthesis of 1, 2 and 3D-biologically useful bMOFs. The 3D-bMOFs of the disclosure are porous and capable of storing, within the pores of the framework, drugs; absorbing biomolecules; being used as a framework for tissue engineering and scaffolds; expansion within the gastrointestinal tract to serve as a dietary supplement; and the like.

The materials described in the disclosure can be tailored as 2D- or 3D-networks depending upon the metal ions, organic linkers and reaction conditions. With selection of the organic linkers, which represents an integral part of the framework, and reaction conditions such as temperature, pH, solvent systems, reactant ratio and reaction time, the desired framework can be achieved.

The disclosure provides a biocompatible metal-organic framework (bMOF) comprising: a plurality of biocompatible metallic cores, each core linked to at least one other core; a plurality of biocompatible linking ligands that connects adjacent cores, and a plurality of pores, wherein the plurality of linked cores defines the pore. In one aspect, the plurality of cores are different. In one aspect. At least two of the cores are different. In another aspect, the plurality of linking ligands are different. In yet another aspect, the porous framework is functionalized to bind an analyte or guest species. In yet another embodiment, the pores may be heterogeneous or homogenous in size.

The disclosure also provides a biocompatible/environmentally friendly metal-organic framework comprising: a plurality of metal clusters, each metal cluster comprising one or more metal ions; and a plurality of non toxic charged multidentate linking ligands that connect adjacent metal clusters. In one embodiment, the linking ligand comprises an alkyl or cycloalkyl group, consisting of 1 to 20 carbon atoms, an aryl group, consisting of 1 to 5 phenyl rings, or an alkyl or aryl amine, consisting of alkyl or cycloalkyl groups having from 1 to 20 carbon atoms or aryl groups consisting of 1 to 5 phenyl rings, and in which multidentate functional groups are covalently bound to the substructure of the ligand. Multidentate functionality can be obtained using a member selected from the group consisting of $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, wherein R is an alkyl group having from 1 to 5 carbon atoms, or an aryl group consisting of 1 to 2 phenyl rings; and, $CH(SH)_2$, $C(SH)_3$, $CH(NH_2)_2$, $C(NH_2)_3$, $CH(OH)_2$, $C(OH)_3$, $CH(CN)_2$, and $C(CN)_3$. In one embodiment, the linking moiety/ligand comprise carboxylic acid functional groups. This disclosure further includes cycloalkyl or aryl substructure that comprise from 1 to 5 rings that include either all carbon or a mixture of carbon, with nitrogen, oxygen, sulfur, boron, phosphorous, silicon and aluminum atoms making up the ring.

In one aspect, each ligand of the plurality of multidentate linking ligands includes two or more carboxylates. In another aspect, the metal ions are selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Cr^{3+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof. In yet a further aspect, the multidentate linking ligand has 6 or more atoms (e.g., twelve or more atoms) that are incorporated in aromatic rings or non-aromatic rings. The one or more multidentate linking ligands can comprise anions of parent compounds selected from the group consisting of citric acid, malic acid, tartaric acid, retinoic acid, pantothenic acid, folic acid, nicitinic acid, oxalic acid, butyric acid, caproic acid, caprylic acid, capric acid, lauric acid, myristic acid, palmitic acid, stearic acid, arachidic acid, behenic acid, myristoleic acid, palmitoleic acid, oleic acid, linoleic acid, alpha-linoleic acid, arachidonic acid, eicosapentaenoic acid, erucic acid, and docosahexaenoic acid.

The disclosure provides a framework comprising a plurality of metal clusters comprising a metal ion and a linking ligand having a general structure selected from the group consisting of:

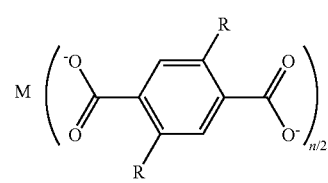

wherein M is a non-toxic metal and R is selected from the group consisting of —H, —OH, —OR1, aryl, substituted aryl, alkyl, substituted alkyl, carboxyl, aminocarbonyl, alkylsulfonylaminocarboxyl, alkoxycarbonyl, and halo, wherein R1 can be —H, and aryl, substituted aryl, alkyl, substituted alkyl, carboxyl, aminocarbonyl, alkylsulfonylaminocarboxyl, alkoxycarbonyl, and halo.

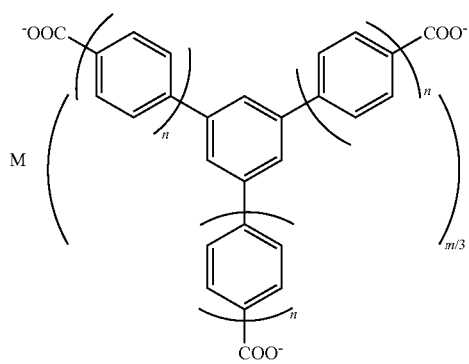
wherein M is a non-toxic metal and wherein n is 0, 1, or 2.
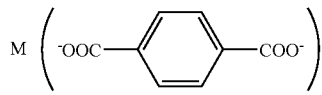
wherein M is a non-toxic metal;
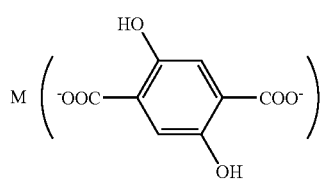
wherein M is a non-toxic metal;
II
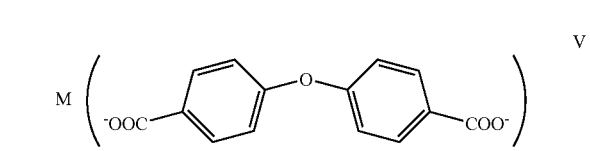
wherein M is a non-toxic metal;
VI
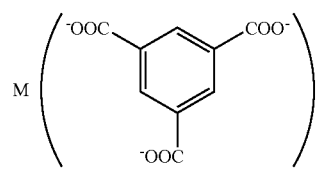
wherein M is a non-toxic metal;
III
IV
V
VII
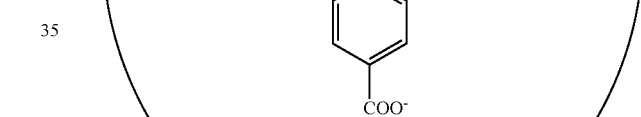
wherein M is a non-toxic metal; and
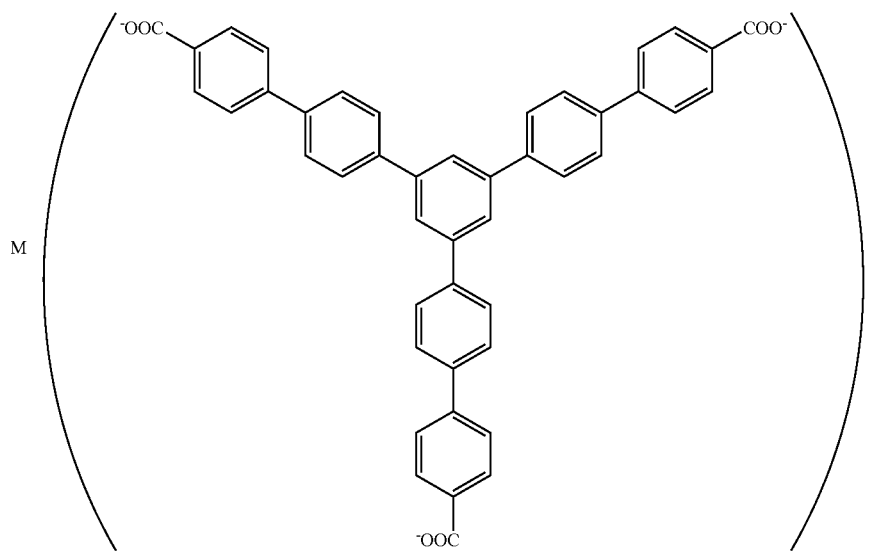
wherein M is a non-toxic metal.

The bMOFs of the disclosure can further comprise a guest species; the guest species can increase the surface area of the MOF. In one aspect, the guest species is a biological agent (e.g., a protein, polypeptide, peptide, lipid, nucleic acid or small molecule agent). In one aspect, the biological agent is a therapeutic agent or a diagnostic agent.

The disclosure also provides a dietary supplement comprising a bMOF of the disclosure. Such bMOFs are biocompatible and can be used for delivery of a drug or other biological agent or adsorption of a biological agent within the gastrointestinal tract. In another embodiment, the bMOF may be rendered expandable by absorption of a guest species within the gastrointestinal tract or made such that the framework is biodegradable during a desired time period there by, for example, giving the stimulus of being satiated.

The disclosure provides a drug delivery composition comprising a bMOF having within its pores a drug, wherein the drug is delivered to the intestinal tract (e.g., an enteric coating).

In yet another aspect, a food additive comprising a bMOF of the disclosure is provided.

The disclosure also provides a gas storage device comprising a MOF of the disclosure.

DETAILED DESCRIPTION

Figure 1:
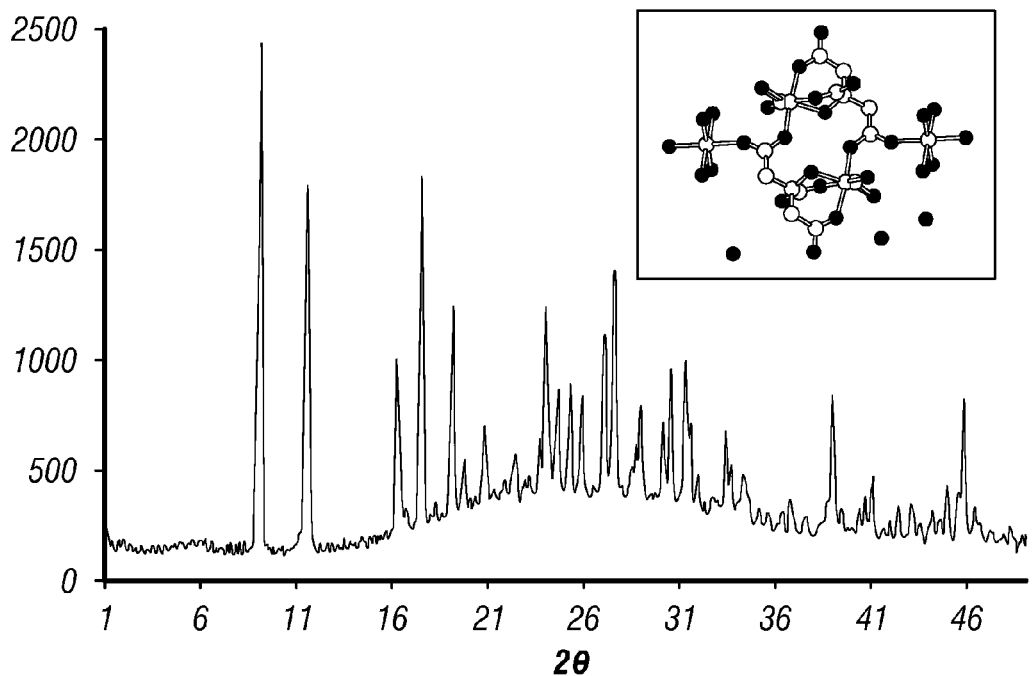
FIG. 1 shows characterization of a MOF of the disclosure.
Figure 1:
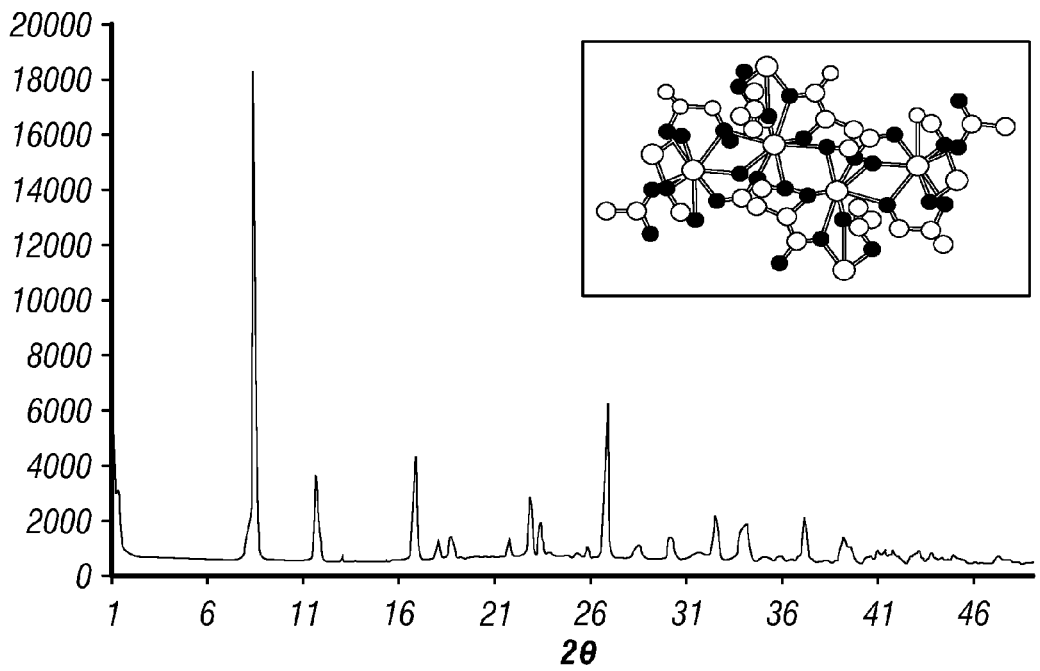

As used herein and in the appended claims, the singular forms "a," "and," and "the" include plural referents unless the context clearly dictates otherwise. Thus, for example, reference to "a framework" includes a plurality of such frameworks and reference to "the composition" includes reference to one or more compositions, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

The use of MOFs comprising non-toxic components as a drug storage and delivery material has not been reported nor the synthesis of biologically non-toxic MOFs. An advantage of the MOFs of the disclosure compared to previous MOFs is the non-toxic nature of the composition. In addition, the MOFs are highly stable with or without the presence of a guest molecule within the pores of the framework.

As used herein, a "cluster" refers to a repeating unit or units found in a framework. Such a framework can comprise a homogenous repeating cluster or a heterogeneous repeating cluster structure. A cluster comprises a transition metal and a linking moiety (sometimes referred to as a linking ligand). A plurality of clusters linked together defines a framework.

A "linking moiety" refers to a mono-dentate, bidentate or multidentate compound that bind a biocompatible metal or a plurality of biocompatible metals, respectively.

As used herein "linking ligand" or "linking moiety" refers to a chemical species (including neutral molecules and ions) that coordinate two or more metals and the definition of void regions or channels in the framework that is produced. The linking ligand of the disclosure is a non-toxic molecule. Examples of a linking ligand useful in the methods and compositions of the disclosure include citric acid, malic acid, and tartaric acid. Other linking moieties or ligands include, for example, methanoic acid, ethanoic acid, propanoic acid, butanoic acid, valeric acid, caproic acid, caprylic acid, capric acid, lauric acid, mylistic acid, palmitic acid, stearic acid, oleic acid, linoleic acid, linolenic acid, cyclohexanecarboxylic acid, phenylacetic acid, benzoic acid, oxalic acid, malonic acid, succinic acid, glutaric acid, adipic acid, pimelic acid, suberic acid, maleic acid, fumaric acid, phthalic acid, isophthalic acid, terephthalic acid, hemimellitic acid, trimellitic acid, trimesic acid, succinic anhydride, maleic anhydride, phthalic anhydride, glycolic acid, lactic acid, hydroxybutyric acid, mandelic acid, glyceric acid, malic acid, tartaric acid, citric acid, and ascorbic acid.

A linking moiety/ligand can comprise an alkyl or cycloalkyl group, consisting of 1 to 20 carbon atoms, an aryl group, consisting of 1 to 5 phenyl rings, or an alkyl or aryl amine, consisting of alkyl or cycloalkyl groups having from 1 to 20 carbon atoms or aryl groups consisting of 1 to 5 phenyl rings, and in which multidentate functional groups are covalently bound to the substructure of the ligand. Multidentate functionality can be selected from the group consisting of $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, wherein R is an alkyl group having from 1 to 5 carbon atoms, or an aryl group consisting of 1 to 2 phenyl rings; and, $CH(SH)_2$, $C(SH)_3$, $CH(NH_2)_2$, $C(NH_2)_3$, $CH(OH)_2$, $C(OH)_3$, $CH(CN)_2$, and $C(CN)_3$. In one embodiment, the linking moiety/ligand comprise carboxylic acid functional groups. This disclosure further includes cycloalkyl or aryl substructure that comprise from 1 to 5 rings that include either all carbon or a mixture of carbon, with nitrogen, oxygen, sulfur, boron, phosphorous, silicon and aluminum atoms making up the ring.

Another aspect of this disclosure provides for crystalline metal-organic microporous materials that can be synthesized by the addition of a solution of a metal salt to a solution containing an appropriate blend of ligands, some of which contain multidentate functional groups, as described herein, and others of which contain monodentate functional groups, in the presence of a suitable templating agent.

In one aspect, the linking ligand comprises one or more carboxylates. For example, the linking ligand may be a polycarboxylic acid. As used herein, the term "polycarboxylic acid" indicates a dicarboxylic, tricarboxylic, tetracarboxylic, pentacarboxylic, and like monomeric polycarboxylic acids, and anhydrides, and combinations thereof, as well as polymeric polycarboxylic acids, anhydrides, copolymers, and combinations thereof.

Illustratively, a monomeric polycarboxylic acid may be a dicarboxylic acid, including, but not limited to, unsaturated aliphatic dicarboxylic acids, saturated aliphatic dicarboxylic acids, aromatic dicarboxylic acids, unsaturated cyclic dicarboxylic acids, saturated cyclic dicarboxylic acids, hydroxy-substituted derivatives thereof, and the like. Or, illustratively, the polycarboxylic acid(s) itself may be a tricarboxylic acid, including, but not limited to, unsaturated aliphatic tricarboxylic acids, saturated aliphatic tricarboxylic acids, aromatic tricarboxylic acids, unsaturated cyclic tricarboxylic acids, saturated cyclic tricarboxylic acids, hydroxy-substituted derivatives thereof, and the like. It is appreciated that any such polycarboxylic acids may be optionally substituted, such as with hydroxy, halo, alkyl, alkoxy, and the like. In one variation, the polycarboxylic acid is the saturated aliphatic tricarboxylic acid, citric acid. Other suitable polycarboxylic acids are contemplated to include, but are not limited to, aconitic acid, adipic acid, azelaic acid, butane tetracarboxylic acid dihydride, butane tricarboxylic acid, chlorendic acid, citraconic acid, dicyclopentadiene-maleic acid adducts, diethylenetriamine pentaacetic acid, adducts of dipentene and maleic acid, ethylenediamine tetraacetic acid (EDTA), fully maleated rosin, maleated tall-oil fatty acids, fumaric acid, glutaric acid, isophthalic acid, itaconic acid, maleated rosin oxidized with potassium peroxide to alcohol then carboxylic acid, maleic acid, malic acid, mesaconic acid, biphenol A or bisphenol F reacted to introduce 3-4 carboxyl groups, oxalic acid, phthalic acid, sebacic acid, succinic acid, tartaric acid, terephthalic acid, tetrabromophthalic acid, tetrachlorophthalic acid, tetrahydrophthalic acid, trimellitic acid, trimesic acid, and the like, and anhydrides, and combinations thereof.

The disclosure provides a cluster comprising a metal ion and a linking ligand having a general structure selected from the group consisting of:

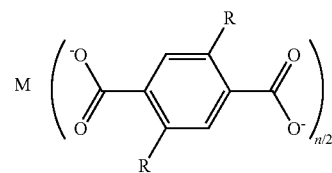

I wherein M is a non-toxic metal and R is selected from the group consisting of —H, —OH, —OR1, aryl, substituted aryl, alkyl, substituted alkyl, carboxyl, aminocarbonyl, alkylsulfonylaminocarboxyl, alkoxycarbonyl, and halo, wherein R1 can be —H, and aryl, substituted aryl, alkyl, substituted alkyl, carboxyl, aminocarbonyl, alkylsulfonylaminocarboxyl, alkoxycarbonyl, and halo.

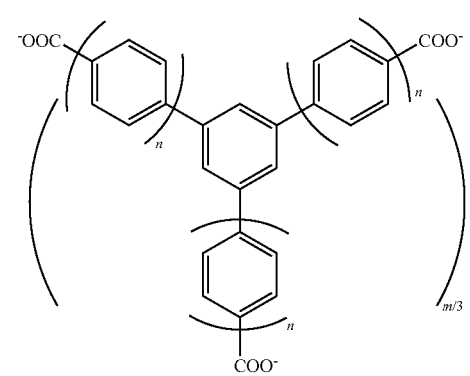

II wherein M is a non-toxic metal and wherein n is 0, 1, or 2.

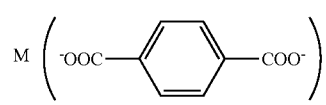

III wherein M is a non-toxic metal;

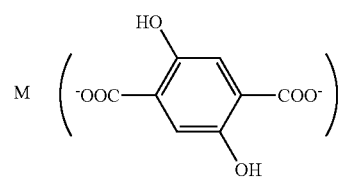

IV wherein M is a non-toxic metal;

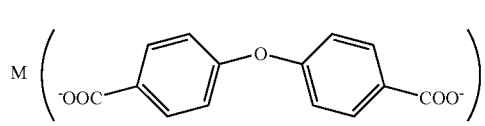

V wherein M is a non-toxic metal;

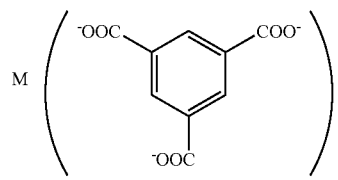

VI wherein M is a non-toxic metal;

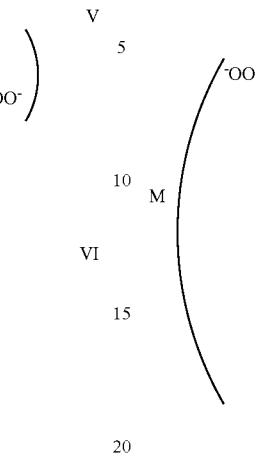

VII wherein M is a non-toxic metal; and

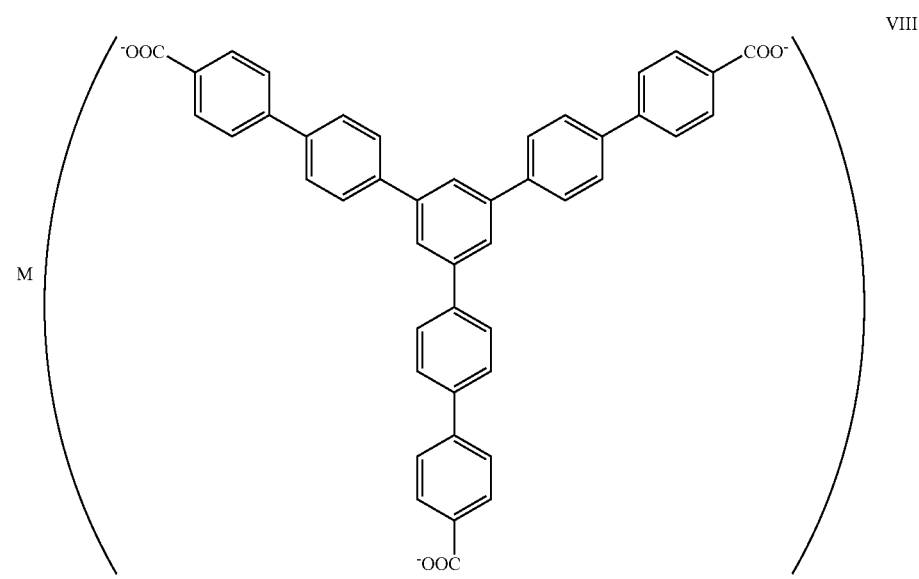

VIII wherein M is a non-toxic metal.

General formulas I-VIII above, depict a cluster comprising a metal ion and a linking moiety, however it will be recognized that the linking moieties can be modified or derivatized. For example, the linking moiety as set forth in Formula II can be modified as follows:

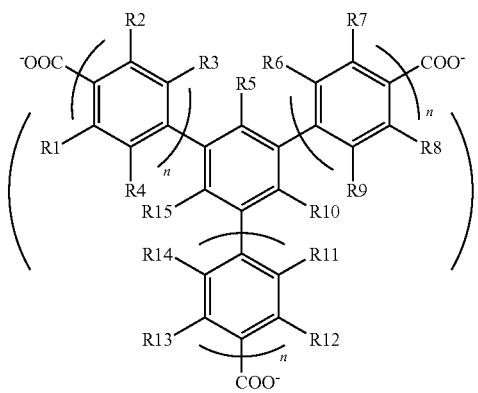

IX wherein each of R1-15 are independently selected from the group consisting of —H, —OH, —OR$^{16}$, aryl, substituted aryl, alkyl, substituted alkyl, carboxyl, aminocarbonyl, alkylsulfonylaminocarboxyl, alkoxycarbonyl, and halo, wherein R$^{16}$ can be —H, and aryl, substituted aryl, alkyl, substituted alkyl, carboxyl, aminocarbonyl, alkylsulfonylaminocarboxyl, alkoxycarbonyl, and halo.

The term "alkyl" refers to a saturated monovalent chain of carbon atoms, which may be optionally branched; the term "cycloalkyl" refers to a monovalent chain of carbon atoms, a portion of which forms a ring; the term "alkenyl" refers to an unsaturated monovalent chain of carbon atoms including at least one double bond, which may be optionally branched; the term "cycloalkenyl" refers to an unsaturated monovalent chain of carbon atoms, a portion of which forms a ring; the term "heterocyclyl" refers to a monovalent chain of carbon and heteroatoms, wherein the heteroatoms are selected from nitrogen, oxygen, and sulfur, a portion of which, including at least one heteroatom, form a ring; the term "aryl" refers to an aromatic mono or polycyclic ring of carbon atoms, such as phenyl, naphthyl, and the like; and the term "heteroaryl" refers to an aromatic mono or polycyclic ring of carbon atoms and at least one heteroatom selected from nitrogen, oxygen, and sulfur, such as pyridinyl, pyrimidinyl, indolyl, benzoxazolyl, and the like. It is to be understood that each of alkyl, cycloalkyl, alkenyl, cycloalkenyl, and heterocyclyl may be optionally substituted with independently selected groups such as alkyl, haloalkyl, hydroxyalkyl, aminoalkyl, carboxylic acid and derivatives thereof, including esters, amides, and nitriles, hydroxy, alkoxy, acyloxy, amino, alkyl and dialkylamino, acylamino, thio, and the like, and combinations thereof. It is further to be understood that each of aryl and heteroaryl may be optionally substituted with one or more independently selected substituents, such as halo, hydroxy, amino, alkyl or dialkylamino, alkoxy, alkylsulfonyl, cyano, nitro, and the like.

The disclosure also provides a biocompatible metal-organic framework (bMOF) comprising a homogenous or heterogeneous plurality of clusters, wherein the clusters form a framework.

A "framework," as used herein, refers to a framework of repeating clusters having a 2-D or 3-D structure.

A non-toxic chemical species refers to a chemical that when contacted with a biological organism does not have, or has limited, direct effect on cell apoptosis or death. Such materials can also be referred to as biologically safe, biologically inert, and biocompatible.

As used herein "non-linking ligand" means a chemical species that is coordinated to a metal but does not act as a linker.

As used herein "guest" means any chemical species that resides within the void regions of an open framework solid that is not considered integral to the framework. Examples include: molecules of the solvent that fill the void regions during the synthetic process, other molecules that are exchanged for the solvent such as during immersion (via diffusion) or after evacuation of the solvent molecules, such as gases in a sorption experiment. A guest species may be a drug, therapeutic agent or diagnostic agent to be "carried" by the framework of the disclosure. A chemical species is used herein to include peptides, polypeptides, nucleic acid molecules, and fatty acids. Typically a drug will comprise a small organic molecule capable of filling or partially filling a void of a framework.

In yet another embodiment, the framework can be used as a scaffold for tissue engineering, wherein the framework may be infiltrate by cells or extracellular matrix material (e.g., collagen, elastin and the like) such that it support cell growth. Because the framework is biocompatible cells can grow and proliferate on the framework.

As used herein "charge-balancing species" means a charged guest species that balances the charge of the framework. Quite often this species is strongly bound to the framework, i.e. via hydrogen bonds. It may decompose upon evacuation to leave a smaller charged species, or be exchanged for an equivalently charged species, but typically it cannot be removed from the pore of a metal-organic framework without collapse.

As used herein "space-filling agent" means a guest species that fills the void regions of an open framework during synthesis. Materials that exhibit permanent porosity remain intact after removal of the space-filling agent via heating and/or evacuation. Examples include: solvent molecules or molecular charge-balancing species. The latter may decompose upon heating, such that their gaseous products are easily evacuated and a smaller charge-balancing species remain in the pore (i.e. protons). Sometimes space filling agents are referred to as templating agents.

As used herein "accessible metal site" means a site in a metal cluster and, in particular, a position adjacent to a metal in a metal cluster available for a chemical moiety such as a ligand to attach.

As used herein "open metal site" means a site in a metal cluster and, in particular, a position adjacent to a metal in a metal cluster from which a ligand or other chemical moiety has been removed, rendering that metal cluster reactive for adsorption of a chemical species having available electron density for attachment to the metal cluster and, in particular, a metal in the metal cluster.

As used herein "metal cluster" means any metal containing moiety present in a bMOF of the disclosure. This definition embracing single metal atoms or metal ions to groups of metals or metal ions that optionally include ligands or covalently bonded groups.

In one embodiment of the disclosure, a vehicle for delivery of a biological agent to an organism comprising a bMOF is provided. The bMOF of the embodiment includes a plurality of metal clusters and a plurality of charged multidentate non-toxic linking ligands that connect adjacent metal clusters. Each metal cluster includes one or more metal ions and at least one open metal site. Advantageously, the bMOF includes one or more sites for capturing/binding molecule to be delivered to an organism (e.g., a mammal, including a human). In this embodiment, the one or more sites include the at least one open metal site. Biological agents that may be captured/stored in the frameworks of the disclosure include any biological molecules capable of fitting within a pore and comprising available electron density for attachment to the one or more sites. Such electron density includes molecules having multiple bonds between two atoms contained therein or molecules having a lone pair of electrons.

In a variation of this embodiment, the open metal site is formed by activating a precursor metal-organic framework. In a refinement, this activation involves removing one or more chemical moieties from the metal cluster. Typically, such moieties are ligands complexed to or bonded to a metal or metal ion within the metal clusters. Moreover, such moieties include species such as water, solvent molecules contained within the metal clusters, and other chemical moieties having electron density available for attachment to the metal cluster and/or metal atoms or ions contained therein. Such electron density includes molecules having multiple bonds between two atoms contained therein or molecules having a lone pair of electrons.

In another embodiment of the disclosure, a biocompatible metal organic framework is provided, the biocompatible metal organic framework comprises a plurality of metal cores and a plurality of charged non-toxic multidentate linking ligands that connect adjacent metal clusters. Each metal core includes one or more metal ions and at least one accessible metal site. The metal ions are typically alkali earth metals and the ligands are biocompatible acids. Advantageously, the metal-organic framework includes one or more sites for binding or storing a biological molecule or gas. In this embodiment, the one or more sites include the at least one accessible metal site. Gases that may be stored in the gas storage material of the disclosure include gas molecules comprising available electron density for attachment to the one or more sites for storing gas. Suitable examples of such gases include, but are not limited to, the gases comprising a component selected from the group consisting of ammonia, argon, carbon dioxide, carbon monoxide, hydrogen, and combinations thereof. In one variation of this embodiment, the accessible metal site is an open metal site.

The metal-organic frameworks used in the embodiments of the disclosure include a plurality of pores for adsorption of a biological molecule or gas. In one variation, the plurality of pores has a unimodal size distribution. In another variation, the plurality of pores have a multimodal (e.g., bimodal) size distribution.

In another variation of the embodiments of the materials set forth above, the metal organic frameworks include metal clusters comprising one or more metal ions. In another variation, the metal-organic frameworks include metal clusters that comprise two or more metal ions. In still another variation, the metal-organic frameworks include metal cores that comprise three or more metal ions. The metal ions can be selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Cr^{3+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof.

An environmentally friendly metal-organic framework of the disclosure comprises a plurality of metal cores, each metal core comprising one or more metal ions; and a plurality of non toxic charged multidentate linking ligands that connect adjacent metal cores. In one aspect, the each ligand of the plurality of multidentate linking ligands includes two or more carboxylates. In yet another aspect, the multidentate linking ligand has twelve or more atoms that are incorporated in aromatic rings or non-aromatic rings. In a further aspect, the one or more multidentate linking ligands comprise anions of parent compounds selected from the group consisting of citric acid, malic acid, tartaric acid, retinoic acid, pantothenic acid, folic acid, nicitinic acid, oxalic acid, butyric acid, caproic acid, caprylic acid, capric acid, lauric acid, myristic acid, palmitic acid, stearic acid, arachidic acid, behenic acid, myristoleic acid, palmitoleic acid, oleic acid, linoleic acid, alpha-linoleic acid, arachidonic acid, eicosapentaenoic acid, erucic acid, and docosahexaenoic acid.

The metal-organic framework used in the disclosure optionally further comprises a non-linking ligand. In a variation, the non-linking ligand is selected from the group consisting of $O^{2-}$, sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, sulfide, hydrogen sulphate, selenide, selenate, hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, iodite, hypoiodite; and combinations thereof.

The metal-organic frameworks of the disclosure optionally further comprise space-filling agents, adsorbed chemical species, guest species, and combinations thereof. In some variations of the disclosure, space-filling agents, adsorbed chemical species and guest species increase the surface area of the metal-organic framework. Suitable space-filling agents include, for example, a component selected from the group consisting of:

(i) alkyl amines and their corresponding alkyl ammonium salts, containing linear, branched, or cyclic aliphatic groups, having from 1 to 20 carbon atoms;

(ii) aryl amines and their corresponding aryl ammonium salts having from 1 to 5 phenyl rings;

(iii) alkyl phosphonium salts, containing linear, branched, or cyclic aliphatic groups, having from 1 to 20 carbon atoms;

(iv) aryl phosphonium salts, having from 1 to 5 phenyl rings;

(v) alkyl organic acids and their corresponding salts, containing linear, branched, or cyclic aliphatic groups, having from 1 to 20 carbon atoms;

(vi) aryl organic acids and their corresponding salts, having from 1 to 5 phenyl rings;

(vii) aliphatic alcohols, containing linear, branched, or cyclic aliphatic groups, having from 1 to 20 carbon atoms;

(viii) aryl alcohols having from 1 to 5 phenyl rings;

(a) inorganic anions from the group consisting of sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, O.sup.2−, diphosphate, sulfide, hydrogen sulphate, selenide, selenate, hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, iodite, hypoiodite, and the corresponding acids and salts of said inorganic anions;

(b) ammonia, carbon dioxide, methane, oxygen, argon, nitrogen, ethylene, hexane, benzene, toluene, xylene, chlorobenzene, nitrobenzene, naphthalene, thiophene, pyridine, acetone, 1,2-dichloroethane, methylenechloride, tetrahydrofuran, ethanolamine, triethylamine, trifluoromethylsulfonic acid, N,N-dimethyl formamide, N,N-diethyl formamide, dimethylsulfoxide, chloroform, bromoform, dibromomethane, iodoform, diiodomethane, halogenated organic solvents, N,N-dimethylacetamide, N,N-diethylacetamide, 1-methyl-2-pyrrolidinone, amide solvents, methylpyridine, dimethylpyridine, diethylethe, and mixtures thereof. Examples of adsorbed chemical species include ammonia, carbon dioxide, carbon monoxide, hydrogen, amines, methane, oxygen, argon, nitrogen, argon, organic dyes, polycyclic organic molecules, flavorants, small molecule therapeutics and diagnostics and combinations thereof. Examples of guest species are organic molecules with a molecular weight less than about 100 g/mol, organic molecules with a molecular weight less than about 300 g/mol, organic molecules with a molecular weight less than about 600 g/mol, organic molecules with a molecular weight greater than about 600 g/mol. In some variations, adsorbed chemical species, guest species, and space-filling agents are introduced in the metal-organic frameworks by contacting the metal-organic frameworks with a pre-selected chemical species, guest species, or space-filling agent. In another variation of the disclosure, the metal organic framework comprises an interpenetrating metal-organic framework that increases the surface area of the metal-organic framework.

In still another embodiment of the disclosure, a method of forming the material set forth above is provided.

The metal-organic framework is formed by combining a solution comprising a solvent and metal ions selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Cr^{3+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof with a multidentate linking ligand to form a percursor bMOF. The multidentate linking ligand can comprise two or more carboxylates or anions of parent compounds selected from the group consisting of citric acid, malic acid, tartaric acid, retinoic acid, pantothenic acid, folic acid, nicitinic acid, oxalic acid, butyric acid, caproic acid, caprylic acid, capric acid, lauric acid, myristic acid, palmitic acid, stearic acid, arachidic acid, behenic acid, myristoleic acid, palmitoleic acid, oleic acid, linoleic acid, alpha-linoleic acid, arachidonic acid, eicosapentaenoic acid, erucic acid, and docosahexaenoic acid.

The bMOFs of the disclosure can be formed by using any of Schemes I or II.

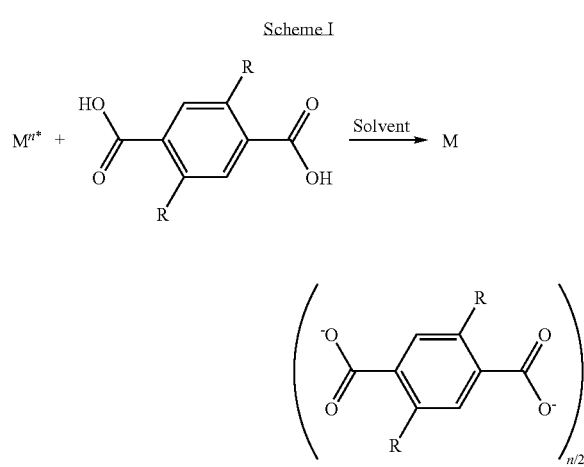

Scheme I

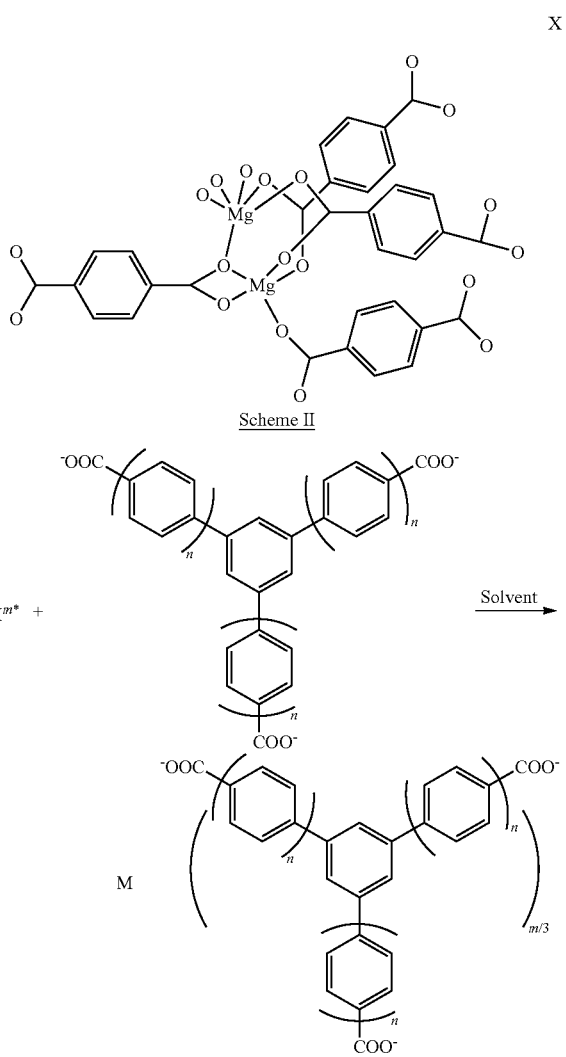

Scheme II wherein M is a nontoxic metal cation. In this embodiment, the linking moiety is shown as being a terephthalic acid or derivative thereof. Using the method of scheme I, a framework as set forth in Formula X, can be generated:

wherein M is a nontoxic metal cation. In this embodiment, the linking moiety is shown as being a trimesic acid or a derivative thereof (n is 1, 2 or 3).

The metal-organic framework used in the disclosure optionally further comprises a non-linking ligand. In a variation, the non-linking ligand is selected from the group consisting of $O_2^-$, sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, sulfide, hydrogen sulphate, selenide, selenate, hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, iodite, hypoiodite; and combinations thereof.

In one variation of the disclosure, the one or more ligands are removed by heating the precursor MOF. Typically, in this variation, the precursor MOF is heated to a temperature from about 30° C. to about 300° C. In another variation, the one or more ligands are removed by exposing the precursor MOF to a vacuum. Typically, the vacuum is characterized by having a pressure less than $10^{-3}$ torr. In other variations, from about $10^{-5}$ torr to about 700 torr. In still another variation of the disclosure, the one or more ligands are removed by simultaneously heating the precursor MOF and by exposing the precursor MOF to a vacuum. In still another variation, the solution used in the method of the disclosure may also include space-filling agents. Examples of suitable space-filling agents are set forth above. In a refinement of each of these variations, one or more ligands of the precursor MOF may be exchanged with another ligand or ligands that are more easily removed by subsequent heating and/or exposure to a vacuum.

In another aspect, the framework set forth above may include an interpenetrating framework that increases the surface area of the framework. Although the frameworks of the disclosure may advantageously exclude such interpenetration, there are circumstances when the inclusion of an interpenetrating framework may be used to increase the surface area.

The frameworks of the disclosure can be used as sorption devices in vitro or in vivo. Sorption is a general term that refers to a process resulting in the association of atoms or molecules with a target material. Sorption includes both adsorption and absorption. Absorption refers to a process in which atoms or molecules move into the bulk of a porous material, such as the absorption of water by a sponge. Adsorption refers to a process in which atoms or molecules move from a bulk phase (that is, solid, liquid, or gas) onto a solid or liquid surface. The term adsorption may be used in the context of solid surfaces in contact with liquids and gases. Molecules that have been adsorbed onto solid surfaces are referred to generically as adsorbates, and the surface to which they are adsorbed as the substrate or adsorbent. Adsorption is usually described through isotherms, that is, functions which connect the amount of adsorbate on the adsorbent, with its pressure (if gas) or concentration (if liquid). In general, desorption refers to the reverse of adsorption, and is a process in which molecules adsorbed on a surface are transferred back into a bulk phase.

The following non-limiting examples illustrate the various embodiments of the disclosure. Those skilled in the art will recognize many variations that are within the spirit of the disclosure and scope of the claims.

EXAMPLES

One (1)-dimensional, 2D- and 3D-environmentally friendly metal organic frameworks (efMOFs or bMOFs) of the disclosure have been synthesized and characterized by PXRD, X-ray signal crystal determinations and TGA. For example, the following synthetic routes can be used to generate certain species of the compositions of the disclosure:

(a) Synthesis of 1D-efMOF:

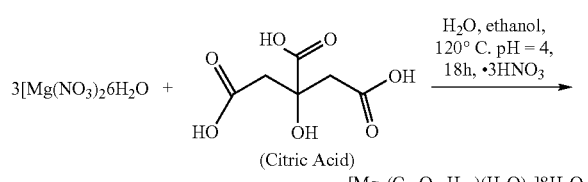

(b) Synthesis of 2D-efMOF:

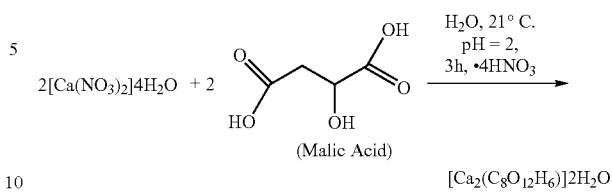

(c) Synthesis of 3D-efMOF:

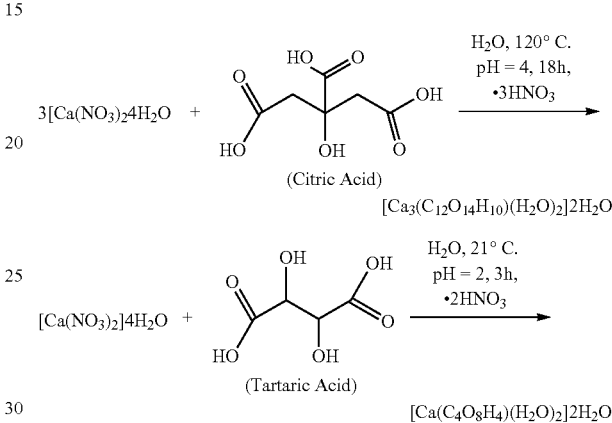

Figure 2:
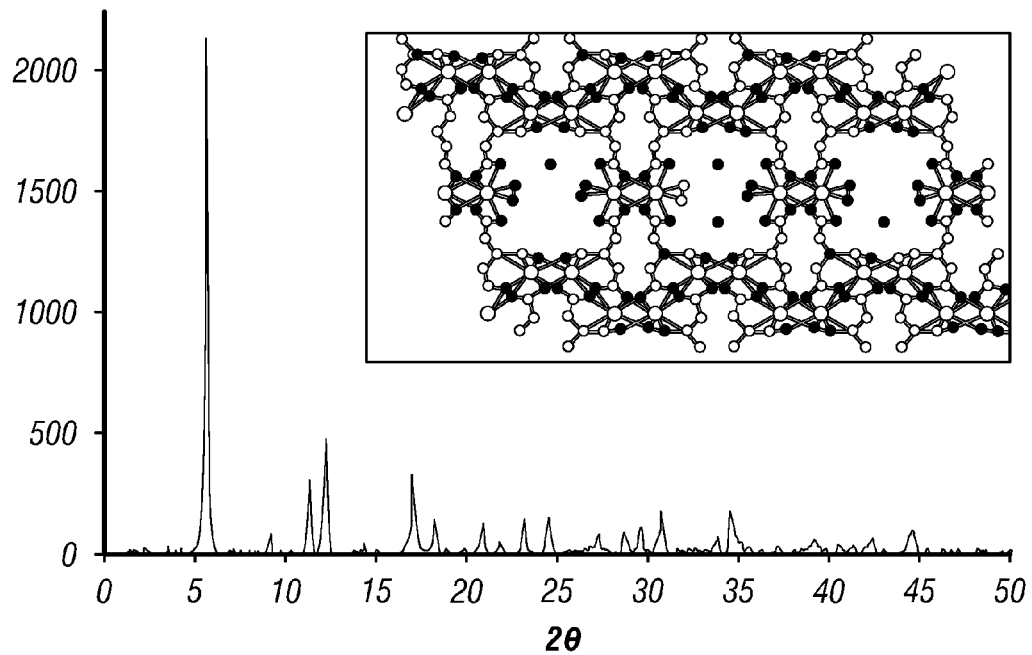
FIG. 2 shows characterization of a MOF of the disclosure.
Figure 2:
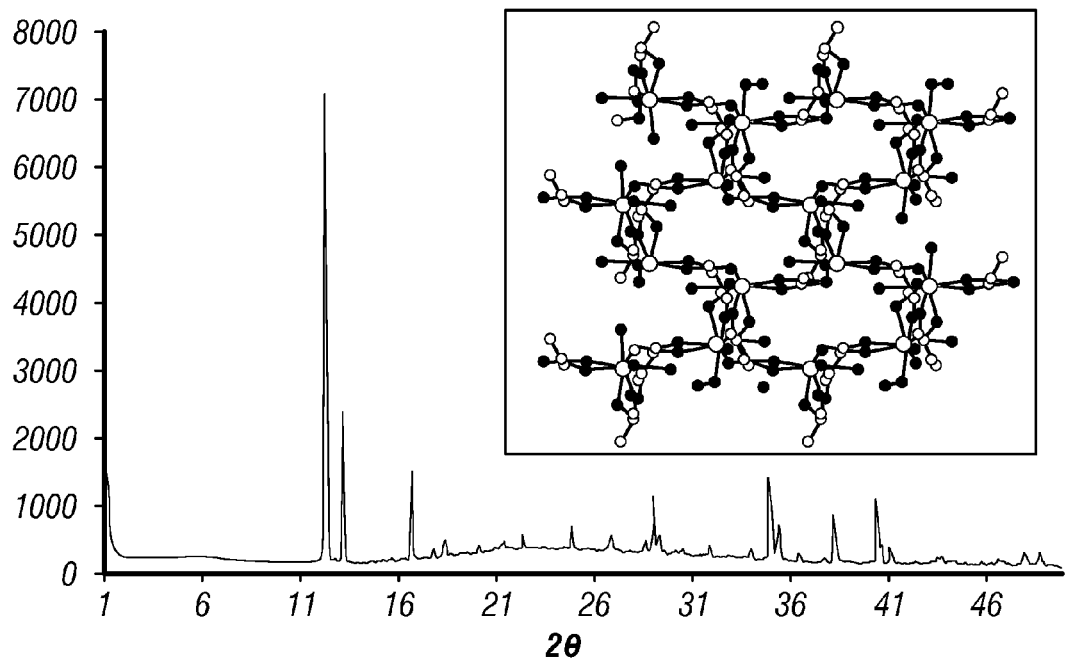

FIG. 1 shows the characterization of $Mg_3(citrate)_2(H_2O)_6 \cdot 8H_2O$ and $Ca(Mal) \cdot 2H_2O$. FIG. 2 shows the characterization of $Ca_3(citrate)_2(H_2O)_2 \cdot 8H_2O$ and $Ca(Tar)(H_2O)_2 \cdot 2H_2O$.

Figure 3A:
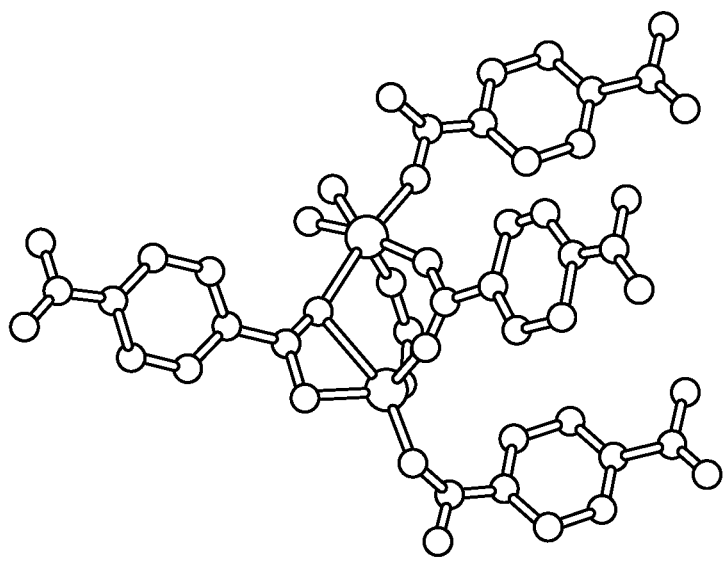
FIG. 3A-B shows a bMOF structure (MgBDC1) of the disclosure. (A) Binuclear cluster in MgBDC-1 including Magnesium; Oxygen; and Carbon atoms. (B) 3D view of MgBDC-1.
Figure 3B:
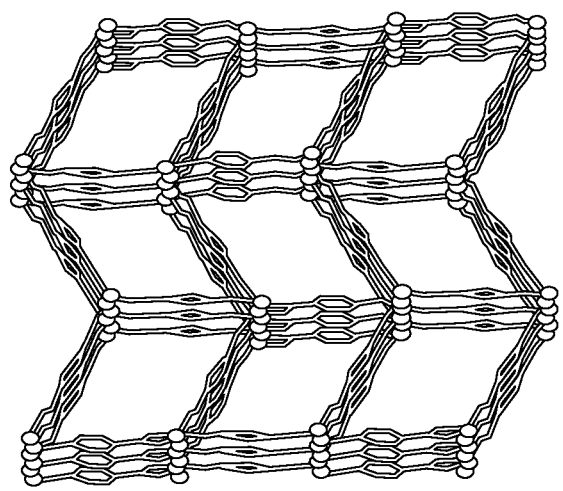

MgBDC-1. A solid mixture of terephthalic acid (H2BDC, 240 mg) and magnesium nitrate hexahydrate $Mg(NO_3)_2 \cdot 6H_2O$ (128 mg) was dissolved in N,N-diethylformamide (13 mL) and 2.0 M aqueous $HNO_3$ solution (40 μL) in a 20-mL vial. 60 μL diisopropylamine and 2 mL DEF was mixed in a 4-mL vial. The 4-mL vial was placed in the 20-mL vial to allow diffusion. The 20-mL vial was capped and placed in an isothermal oven at 85° C. for 72 h. FIG. 3 shows a framework of MgBDC-1.

Figure 4A:
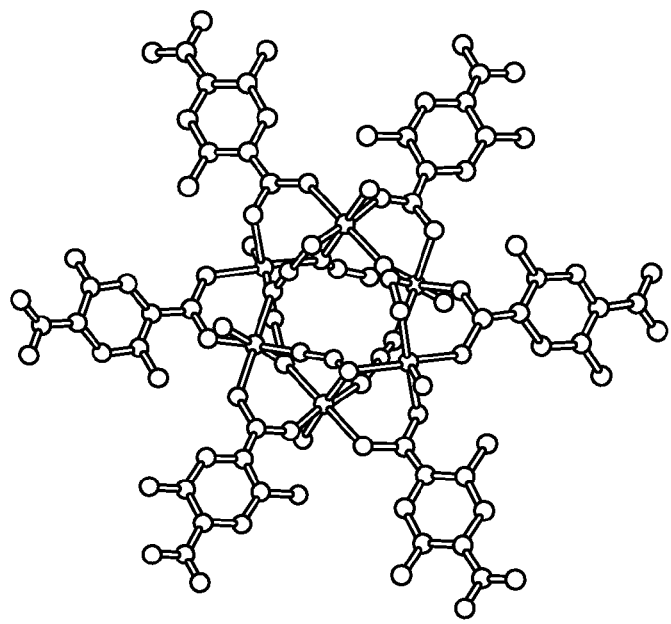
FIG. 4A-B shows a bMOF structure (MgDHBDC-1) of the disclosure (A) Hexanuclear cluster in MgDHBDC-1 including Magnesium; Oxygen; and Carbon atoms. (B) 3D view of MgDHBDC-1.
Figure 4B:
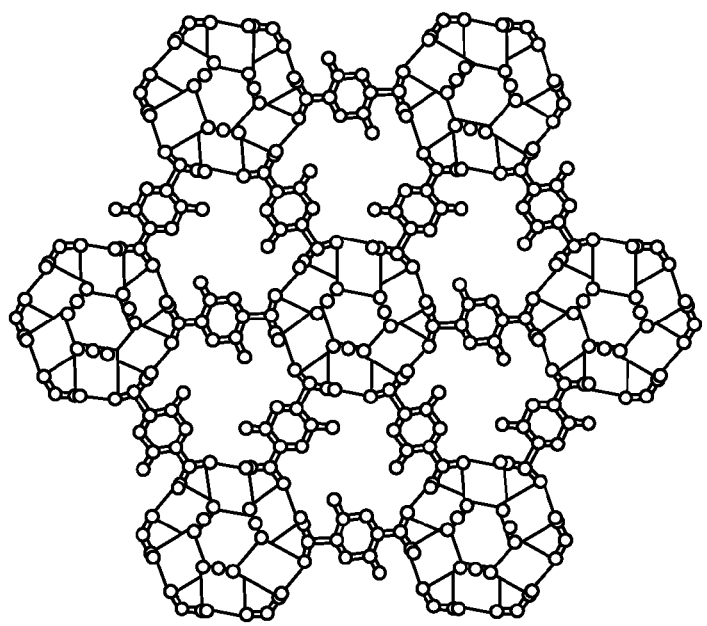

MgDHBDC-1. A solid mixture of 2,5-dihydroxyterephthalic acid (H2DHBDC, 40 mg) and magnesium nitrate hexahydrate $Mg(NO_3)_2 \cdot 6H_2O$ (150 mg) was dissolved in a mixture of N,N-diethylformamide (8 mL), distilled water (1 mL) and 2.0 M aqueous $HNO_3$ solution (20 μL) in a 20-mL vial. 20 μL diisopropylamine and 2 mL N,N-diethylformamide was mixed in a 4-mL vial. The 4-mL vial was placed in the 20-mL vial to allow diffusion. The 20-mL vial was capped and placed in an isothermal oven at 65° C. for 60 days. FIG. 4 shows a framework of MgDHBD-1.

Figure 5:
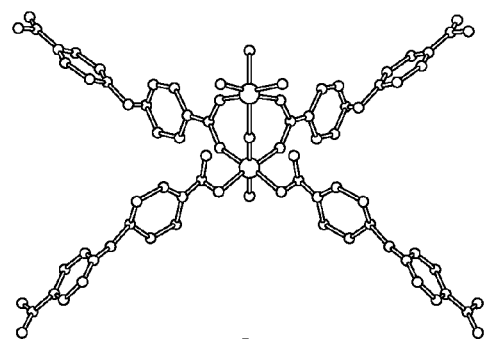
FIG. 5 shows an MgOBA-1 structure of the disclosure including Magnesium; Oxygen; and Carbon atoms.

MgOBA-1. A solid mixture of 4,4'-oxybis(benzoic acid) (H2OBA, 50.0 mg) and magnesium nitrate hexahydrate $Mg(NO_3)_2 \cdot 6H2O$ (10.0 mg) was dissolved in N,N-dimthylformamide (5 mL) in a 20-mL vial. 20 μL diisopropylamine and 2 mL N,N-dimthylformamide was mixed in a 4-mL vial. The 4-mL vial was placed in the 20-mL vial to allow diffusion. The 20-mL vial was capped and placed in an isothermal oven at 65° C. for 10 days. FIG. 5 shows a framework of MgOBA-1.

Figure 6A:
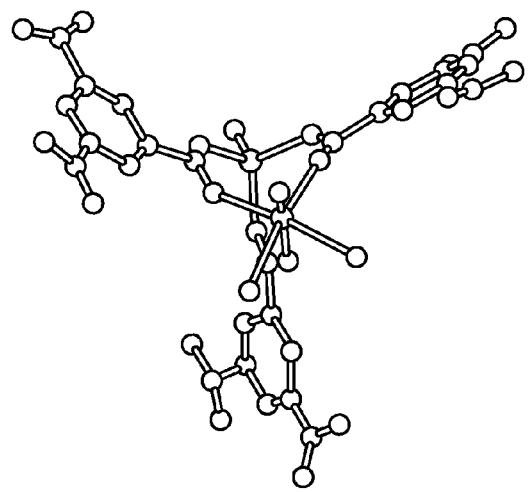
FIG. 6A-B shows a bMOF structure of the disclosure (Mg-BTC-1). (A) shows a binuclear cluster of MgBTC-1 including Magnesium; Oxygen; and Carbon. (B) shows Trigonal links are represented as dark triangles, while light gray triangles represent inorganic SBUs. Empty spaces are illustrated as spheres.
Figure 6B:
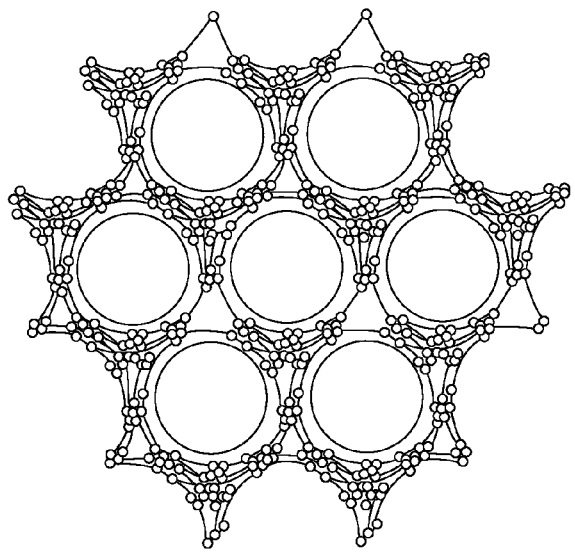

MgBTC-1. A solid mixture of trimesic acid (H3BTC, 50.0 mg) and magnesium nitrate hexahydrate $Mg(NO_3)_2.6H_2O$ (150.0 mg) was dissolved in a mixture of N,N-diethylformamide (5 mL), ethanol (3 mL) and 2-ethyl-1-hexanol (3 mL) in a 20-mL vial. The vial was capped and placed in an isothermal oven at 85° C. for 3 days. FIG. 6 shows a framework of MgBTC-1.

Figure 7:
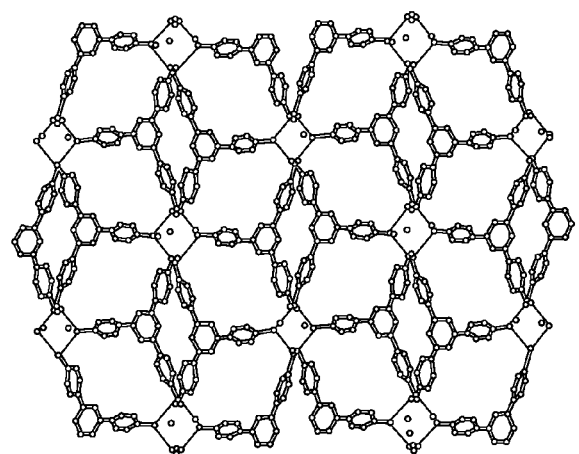
FIG. 7 shows a bMOF (MgBTB-1) framework of the disclosure. An Octahedral Inorganic SBUs and tritopic links form 2D layer structure.

MgBTB-1. A solid mixture of 1,3,5-tri(4'-carboxy-4,4'-biphenyl)benzene (H3BTB, 43.5 mg) and magnesium acetate tetrahydrate $Mg(OAc)_2.4H_2O$ (5.0 mg) was dissolved in a mixture of N,N-dimethylacetatmide (3 mL) and dimethylamine (20 μL) in a 4-mL vial. The vial was capped and placed in an isothermal oven at 120° C. for 3 days. FIG. 7 shows a framework of MgBTB-1.

Figure 8A:
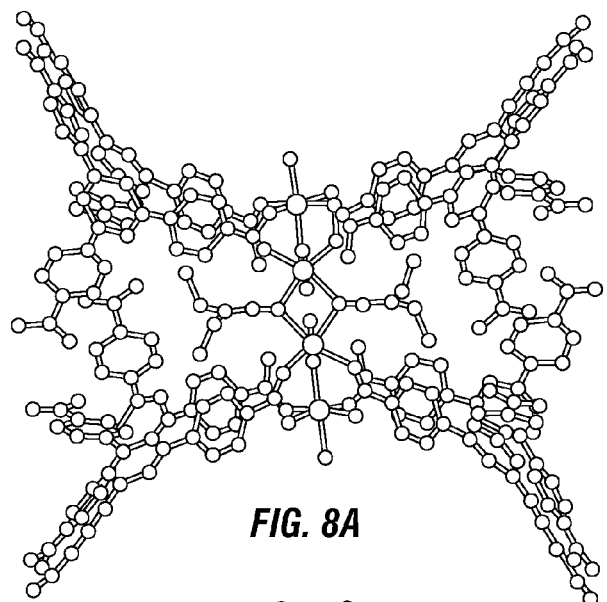
FIG. 8A-B shows a bMOF structure of the disclosure (Mg-BTB-2). (A) Fundamental building units of MgBTB-2 including Magnesium; Oxygen; Carbon; and Nitrogen. (B) Trigonal links are represented as triangles, while cubes represent inorganic SBUs. Empty spaces are illustrated as spheres.
Figure 8B:
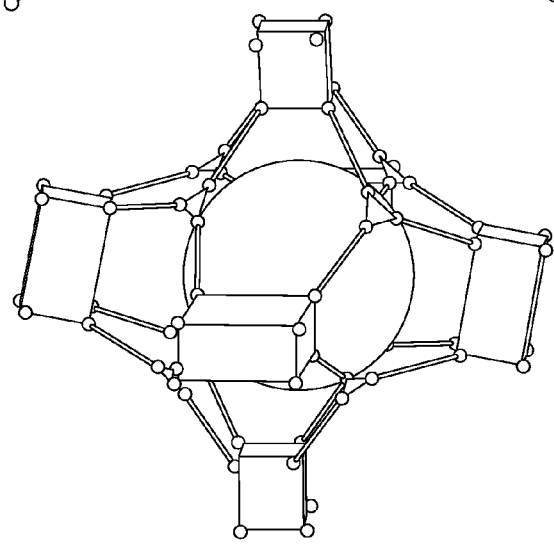

MgBTB-2. A solid mixture of 4,4',4"-benzene-1,3,5-triyl-tri-benzoic acid (H3BTB, 10.0 mg) and magnesium nitrate hexahydrate $Mg(NO_3)_2.6H_2O$ (6.0 mg) was dissolved in a mixture of N,N-diethylformamide (2.5 mL) and distilled water (0.50 mL) in a 4-mL vial. The vial was capped and placed in an isothermal oven at 100° C. for 7 days. FIG. 8 shows a framework of MgBTB-2.

Figure 9A:
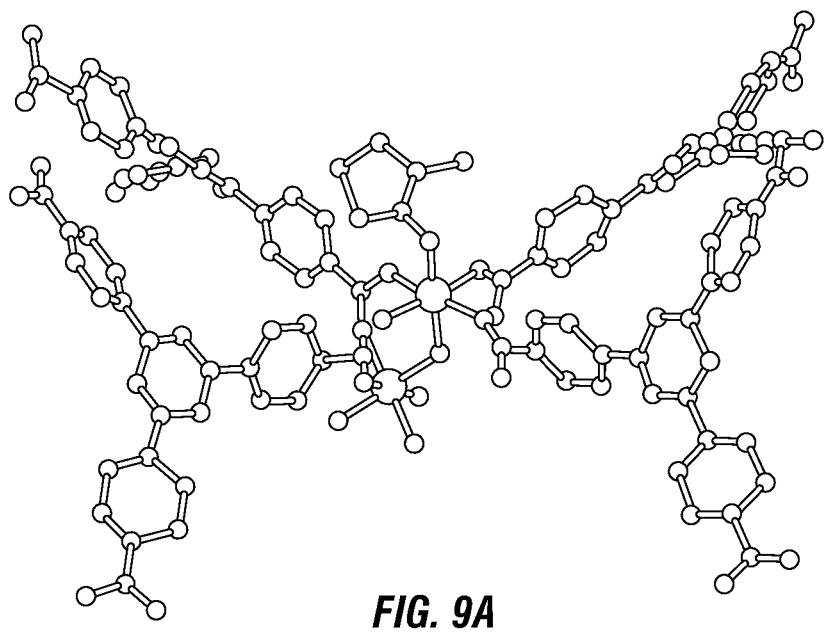
FIG. 9A-B shows a bMOF of the disclosure (MgBTB-3). (A) Fundamental building units of MgBTB-3 including Magnesium; Oxygen; Carbon; and Nitrogen. (B) Inorganic SBUs are represented as squares. Empty spaces are illustrated as spheres.
Figure 9B:
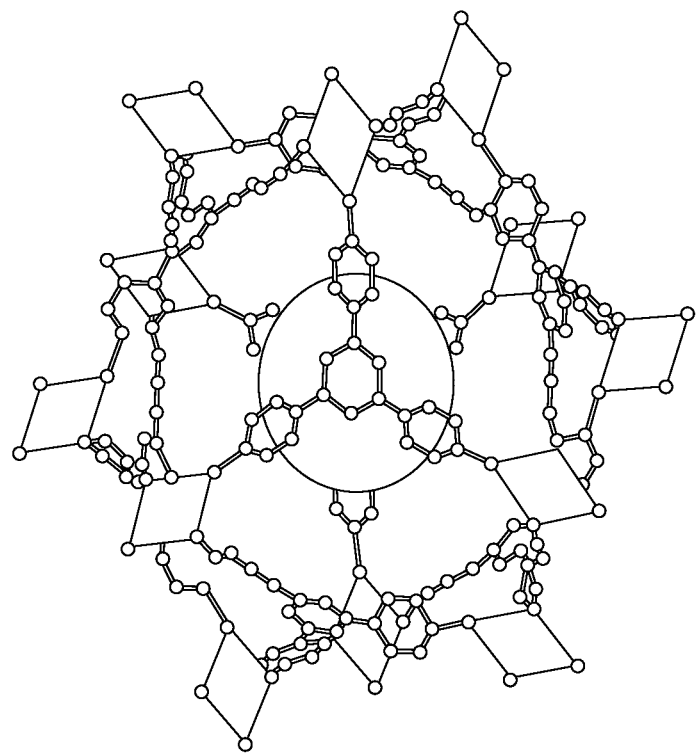

MgBTB-3. A solid mixture of 4,4',4"-benzene-1,3,5-triyl-tri-benzoic acid (H3BTB, 10.0 mg) and magnesium acetate tetrahydrate $Mg(OAc)_2.4H_2O$ (5.0 mg) was dissolved in a mixture of N-methylpyrrolidone (2 mL) and distilled water (1 mL) in a 20-mL vial. 20 μL triethylamine and 2 mL N-methylpyrrolidone was mixed in a 4-mL vial. The 4-mL vial was placed in the 20-mL vial to allow diffusion. The 20-mL vial was capped and placed in an isothermal oven at 65° C. for 7 days. FIG. 9 shows a framework of MgBTB-3.

Figure 10:
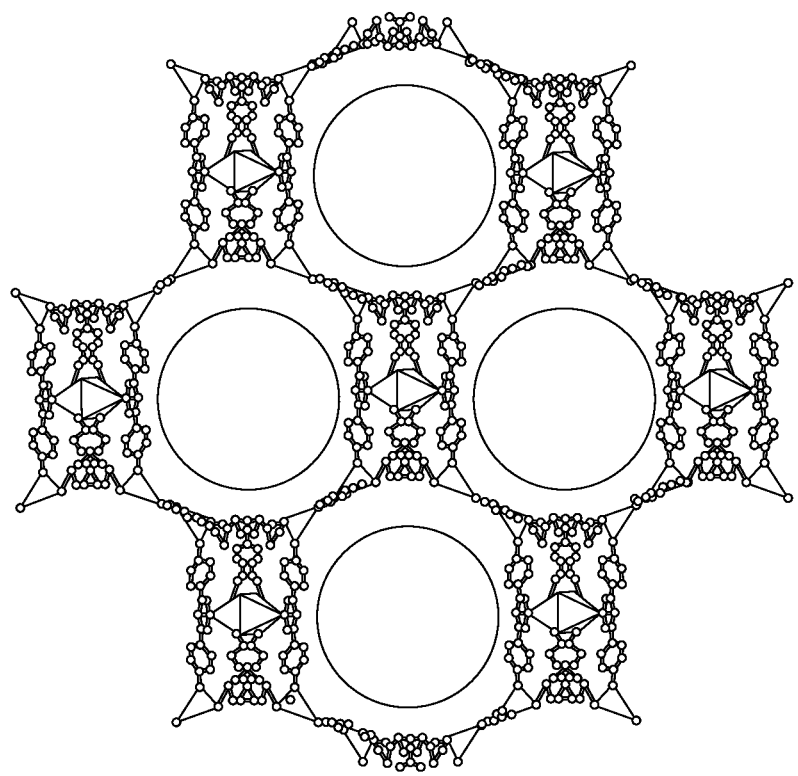
FIG. 10 shows a bMOF of the disclosure (MgBTB-4). The structure consists of two types of inorganic SBUs (light and dark triangles and octahedra) and trigonal links. Empty spaces are illustrated as spheres.

MgBTB-4. A solid mixture of 4,4',4"-benzene-1,3,5-triyl-tri-benzoic acid (H3BTB, 30.0 mg) and magnesium acetate tetrahydrate $Mg(OAc)_2.4H_2O$ (40.0 mg) was dissolved in a mixture of N,N-diethylformamide (10 mL) and 2.0 M aqueous HNO3 solution (120 μL) in a 20-mL vial. 10 μL N,N-diisopropylamine and 2 mL N,N-diethylformamide was mixed in a 4-mL vial. The 4-mL vial was placed in the 20-mL vial to allow diffusion. The 20-mL vial was capped and placed in an isothermal oven at 65° C. for 7 days. FIG. 10 shows a framework of MgBTB-5.

Figure 11A:
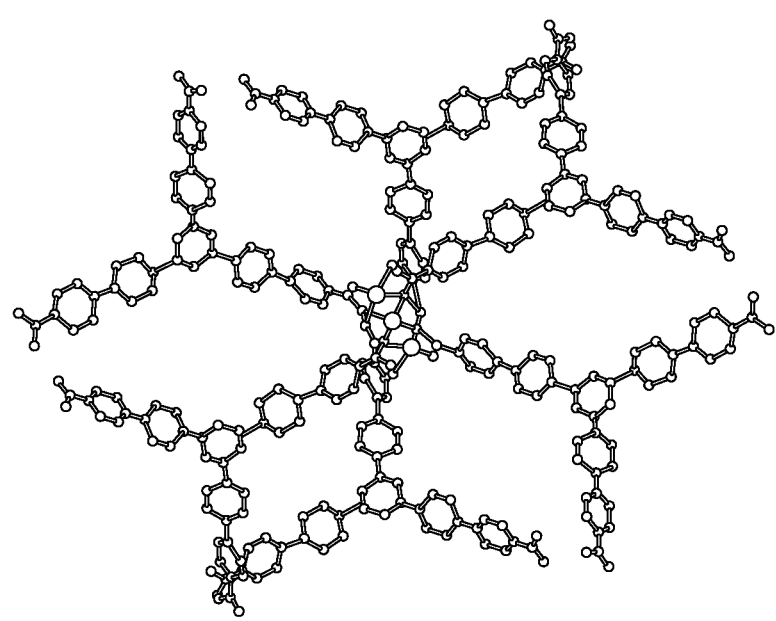
FIG. 11A-B shows yet another bMOF of the disclosure (MgBBC-1). Trinuclear cluster of MgBBC-1 including Magnesium; Oxygen; and Carbon. (B) shows a space fill model of the 2D structure.
Figure 11B:
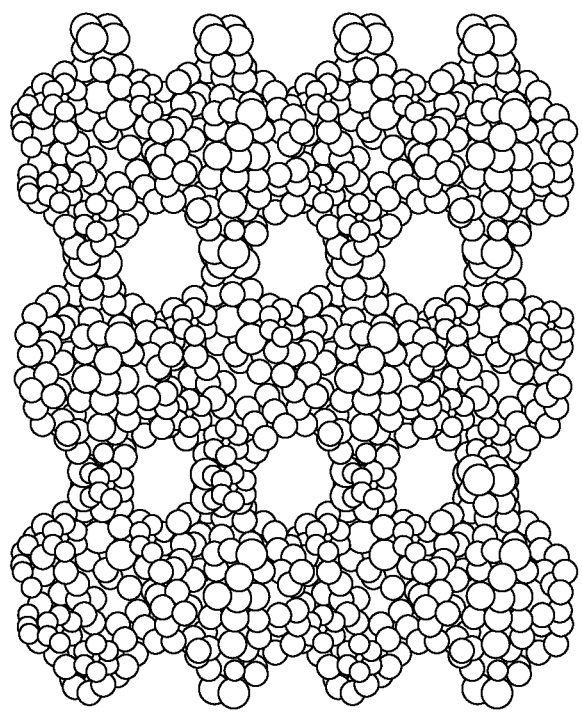

MgBBC-1. A solid mixture of 4,4',4"-benzene-1,3,5-triyl-tri-biphenylcarboxylic acid (H3BBC, 30.0 mg) and magnesium nitrate hexahydrate $Mg(NO_3)_2.6H_2O$ (4.0 mg) was dissolved in a mixture of N,N-diethylformamide (1.5 mL), distilled water (0.30 mL) and 2M aqueous $HNO_3$ solution (20 μL) in a 4-mL vial. The vial was capped and placed in an isothermal oven at 100° C. for 5 days. FIG. 11 shows a framework of MgBBC-1.

Although a number of embodiments and features have been described above, it will be understood by those skilled in the art that modifications and variations of the described embodiments and features may be made without departing from the teachings of the disclosure or the scope of the disclosure as defined by the appended claims.

What is claimed is:

1. A biocompatible metal-organic framework (bMOF) comprising:
   a plurality of biocompatible metallic cores;
   a plurality of biocompatible organic linking ligands that covalently connect adjacent biocompatible metallic cores of the plurality of biocompatible metallic cores, and
   a plurality of pores, wherein the plurality of linked biocompatible metallic cores defines the pores,
   wherein the biocompatible metallic cores comprise a metal ion selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Mo^{3+}$, $W^{3+}$, $Mn^{3+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof, and
   wherein the organic linking ligands comprise anions of parent compounds selected from the group consisting of citric acid, malic acid, tartaric acid, and folic acid.

2. The bMOF of claim 1, wherein the plurality of biocompatible metallic cores are heterogeneous.

3. The bMOF of claim 1, wherein the plurality of organic linking ligands are heterogeneous.

4. The bMOF of claim 1, wherein each ligand of the plurality of multidentate linking ligands includes two or more carboxylates.

5. The bMOF of claim 1 further comprising a guest species.

6. The bMOF of claim 5, wherein the guest species increase the surface area of the bMOF.

7. The bMOF of claim 5, wherein the guest species is biological agent.

8. The bMOF of claim 7, wherein the biological agent is a protein, lipid, nucleic acid or small molecule agent.

9. The bMOF of claim 7, wherein the biological agent is a therapeutic agent.

10. The bMOF of claim 7, wherein the biological agent is a diagnostic agent.

11. The bMOF of claim 1, further comprising interpenetrating bMOFs that increases the surface area.

12. The bMOF of claim 1, further comprising an adsorbed chemical species.

13. The bMOF of claim 12, wherein the adsorbed chemical species is selected from the group consisting of ammonia, carbon dioxide, carbon monoxide, hydrogen, amines, methane, oxygen, argon, nitrogen, argon, organic dyes, polycyclic organic molecules, and combinations thereof.

TABLE A

Summary of Magnesium based edible MOF structures

| Compound Name | Space group | a(Å) | b(Å) | c(Å) | α(°) | β(°) | γ(°) | Dimension |
|---|---|---|---|---|---|---|---|---|
| MgBDC-1 | C2/c | 39.79 | 9.04 | 18.58 | 90.00 | 117.19 | 90.00 | 3D |
| MgDHBDC-1 | R-3 | 27.16 | 27.16 | 9.25 | 90.00 | 90.00 | 120.00 | 3D |
| MgOBA-1 | P2(1)/n | 18.33 | 20.34 | 24.52 | 90.00 | 90.00 | 90.00 | 2D |
| MgBTC-1 | P2(1)/3 | 14.49 | 14.49 | 14.49 | 90.00 | 90.00 | 90.00 | 3D |
| MgBTB-1 | P21/c | 12.45 | 25.80 | 27.48 | 90.00 | 99.36 | 90.00 | 2D |
| MgBTB-2 | R-3 | 38.38 | 38.38 | 47.01 | 90.00 | 90.00 | 120.00 | 3D |
| MgBTB-3 | R-3 | 39.60 | 39.60 | 22.79 | 90.00 | 90.00 | 120.00 | 3D |
| MgBTB-4 | C2/c | 46.28 | 38.69 | 33.24 | 90.00 | 94.19 | 90.00 | 3D |
| MgBBC-1 | C2/c | 41.01 | 24.05 | 15.23 | 90.00 | 95.02 | 90.00 | 2D |

14. A dietary supplement comprising a bMOF of claim 1.

15. A drug delivery agent comprising the bMOF of claim 1.

16. A gas storage device comprising a bMOF of claim 1.

17. A method of making an environmentally friendly metal organic framework, comprising:
reacting a plurality of metal clusters, each metal cluster comprising one or more metal ions selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Mo^{3+}$, $W^{3+}$, $Mn^{3+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof with one or more non toxic charged multidentate organic linking ligands that connect adjacent metal clusters,
wherein the organic linking ligands comprise anions of parent compounds selected from the group consisting of citric acid, malic acid, tartaric acid, and folic acid.

18. A porous framework material comprising a plurality of biocompatible metallic cores, each core comprising one or more metal ions selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Mo^{3+}$, $W^{3+}$, $Mn^{3+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof, wherein each core is linked to at least one other core through a plurality of biocompatible organic linking ligands,
wherein the linking ligand comprises at least two carboxylates, and a plurality of pores,
wherein the plurality of linked cores defines the pores, and
wherein the framework material further comprises one or more drugs within the pores of the framework, wherein the drug is a peptide, polypeptide, protein, nucleic acid, fatty acid or small organic molecule.

19. The porous framework material of claim 18, wherein the organic linking ligand is selected from the group consisting of citrate, malate, and tartrate.

20. The porous framework material of claim 18, wherein the organic linking ligand is selected from the group consisting of malonate, succinate, glutarate, adipate, pimelate, suberate, maleate, fumarate, phthalate, isophthalate, terephthalate, hemimellitate, trimellitate, trimesate, malate, tartarate, and citrate.

21. The porous framework material of claim 18, wherein the organic linking ligand is selected from the group consisting of aldarate, malonate, malate, succinate, glutarate, adipate, tricarboxylates, isocitrate, aconitate, and propane-1,2,3-tricarboxylate (tricarballylate, and carballylate).

22. The porous framework material of claim 18, wherein the framework comprises repeating units having a general formula:

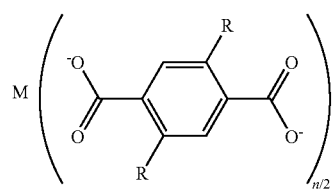

I wherein M is a non-toxic metal ion selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Mo^{3+}$, $W^{3+}$, $Mn^{3+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof, and R is selected from the group consisting of —H, —OH, —OR1, aryl, substituted aryl, alkyl, substituted alkyl, carboxyl, aminocarbonyl, alkylsulfonylaminocarboxyl, alkoxycarbonyl, and halo, wherein R1 can be —H, and aryl, substituted aryl, alkyl, substituted alkyl, carboxyl, aminocarbonyl, alkylsulfonylaminocarboxyl, alkoxycarbonyl, and halo.

23. The porous framework material of claim 18, wherein the framework comprises repeating units having a general formula:

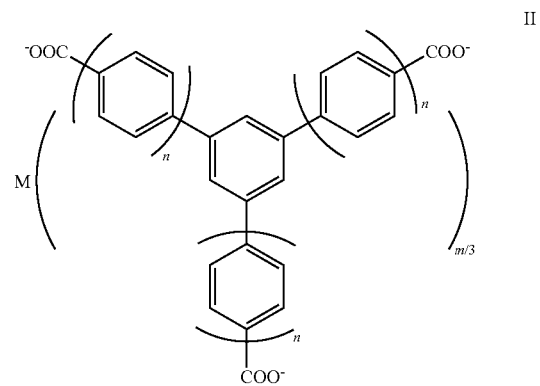

II wherein M is a non-toxic metal ion selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Mo^{3+}$, $W^{3+}$, $Mn^{3+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof, and wherein n is 0, 1, or 2.

24. The porous framework material of claim 18, wherein the framework comprises repeating units having a general formula:

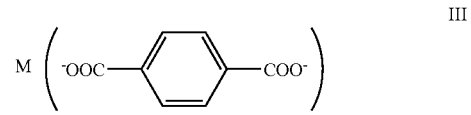

III wherein M is a non-toxic metal ion selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Mo^{3+}$, $W^{3+}$, $Mn^{3+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof.

25. The porous framework material of claim 18, wherein the framework comprises repeating units having a general formula:

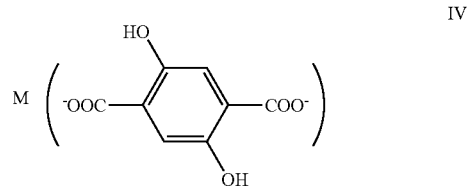

IV wherein M is a non-toxic metal ion selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Mo^{3+}$, $W^{3+}$, $Mn^{3+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof.

26. A porous framework material comprising a plurality of biocompatible metallic cores, each core linked to at least one other core; a plurality of biocompatible linking ligands that connects adjacent cores, wherein the linking ligand comprises at least two carboxylates, and a plurality of pores, wherein the plurality of linked cores defines the pores and a biological molecule chemically attached to a surface of pores of the porous framework, wherein the framework comprises repeating units having a general formula:

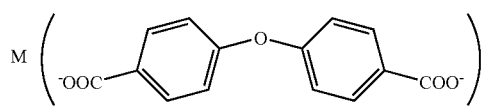

V wherein M is a non-toxic metal.

27. The porous framework material of claim 18, wherein the framework comprises repeating units having a general formula:

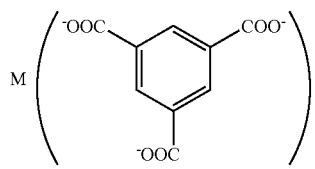

VI wherein M is a non-toxic metal ion selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Mo^{3+}$, $W^{3+}$, $Mn^{3+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof.

28. The porous framework material of claim 18, wherein the framework comprises repeating units having a general formula:

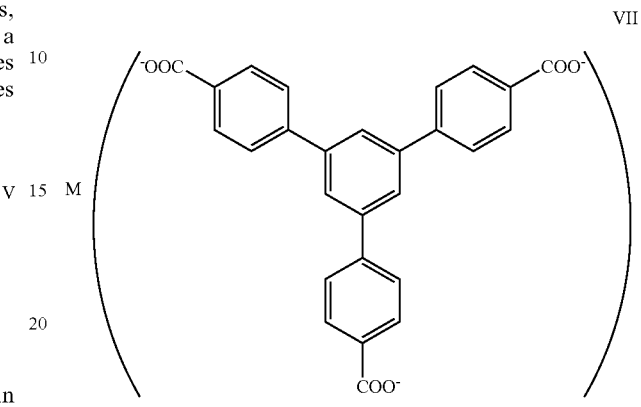

VII wherein M is a non-toxic metal ion selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Mo^{3+}$, $W^{3+}$, $Mn^{3+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof.

29. A porous framework material comprising a plurality of biocompatible metallic cores, each core linked to at least one other core; a plurality of biocompatible linking ligands that connects adjacent cores, wherein the linking ligand comprises at least two carboxylates, and a plurality of pores, wherein the plurality of linked cores defines a pore and a biological molecules chemically attached to a surface of pores of the porous framework, wherein the framework comprising repeating units having a general formula:

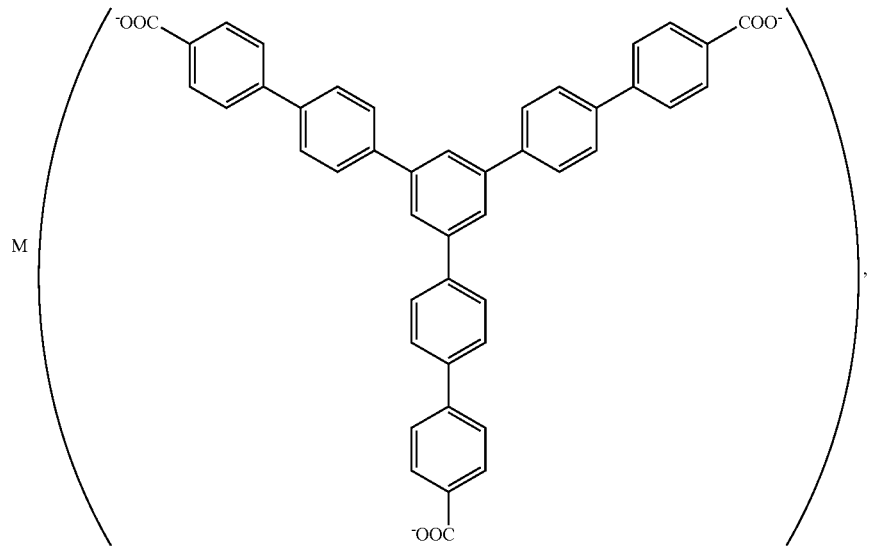

wherein M is a non-toxic metal.

30. The porous framework material of claim 18, wherein the framework comprises a metaloxide of a metal ion selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Mo^{3+}$, $W^{3+}$, $Mn^{3+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof.

31. The porous framework material of claim 18, wherein the biocompatible linking ligand comprises an alkyl or cycloalkyl group, consisting of 1 to 20 carbon atoms, an aryl group, consisting of 1 to 5 phenyl rings, or an alkyl or aryl amine, consisting of alkyl or cycloalkyl groups having from 1 to 20 carbon atoms or aryl groups consisting of 1 to 5 phenyl rings, and wherein a multidentate functional group is covalently bound to the ligand.

32. The porous framework material of claim 31, wherein the multidentate functional group can be selected from the group consisting of $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, wherein R is an alkyl group having from 1 to 5 carbon atoms, or an aryl group consisting of 1 to 2 phenyl rings; and, $CH(SH)_2$, $C(SH)_3$, $CH(NH_2)_2$, $C(NH_2)_3$, $CH(OH)_2$, $C(OH)_3$, $CH(CN)_2$, and $C(CN)_3$.

33. A dietary supplement comprising a porous framework material of claim 20.

34. A method for delivery a drug to a subject comprising administering the porous framework of claim 20 to a subject.

* * * * *